United States Patent
Hilfiker et al.

(10) Patent No.: US 8,570,513 B2
(45) Date of Patent: Oct. 29, 2013

(54) ELLIPSOMETRIC INVESTIGATION AND ANALYSIS OF TEXTURED SAMPLES

(75) Inventors: James N. Hilfiker, Lincoln, NE (US); Jianing Sun, Lincoln, NE (US); Ping He, Lincoln, NE (US); Martin M. Liphardt, Lincoln, NE (US)

(73) Assignee: J.A. Woollam Co., Inc., Lincoln, NE (US)

(*) Notice: Subject to any disclaimer, the term of this patent is extended or adjusted under 35 U.S.C. 154(b) by 134 days.

(21) Appl. No.: 13/373,037

(22) Filed: Nov. 3, 2011

(65) Prior Publication Data

US 2012/0057158 A1 Mar. 8, 2012

Related U.S. Application Data

(60) Continuation-in-part of application No. 12/315,898, filed on Dec. 8, 2008, now Pat. No. 8,059,276, and a division of application No. 12/075,956, filed on Mar. 14, 2008, now Pat. No. 7,830,512, said application No. 12/315,898 is a continuation-in-part of application No. 11/980,262, filed on Oct. 30, 2007, now Pat. No. 7,619,752, which is a continuation-in-part of application No. 11/495,130, filed on Jul. 29, 2006, now Pat. No. 7,333,198, and a division of application No. 11/177,207, filed on Jul. 8, 2005, now Pat. No. 7,084,978, and a continuation-in-part of application No. 10/652,696, filed on Sep. 2, 2003, now Pat. No. 7,230,699, application No. 13/373,037, which is a continuation-in-part of application No. 11/145,470, filed on Jun. 6, 2005, now Pat. No. 7,327,456, which is a continuation-in-part of application No. 10/376,677, filed on Feb. 28, 2003, now Pat. No. 6,982,792.

(60) Provisional application No. 61/126,233, filed on May 2, 2008, provisional application No. 60/459,690, filed on Apr. 3, 2003, provisional application No. 60/588,315, filed on Jul. 15, 2004.

(51) Int. Cl.
*G01J 4/00* (2006.01)

(52) U.S. Cl.
USPC .......................................... 356/364; 356/369

(58) Field of Classification Search
USPC ............................. 356/364, 369; 250/559.09
See application file for complete search history.

(56) References Cited

U.S. PATENT DOCUMENTS

| | | | |
|---|---|---|---|
| 4,373,817 A | 2/1983 | Coates | 356/636 |
| 5,045,704 A | 9/1991 | Coates | 250/372 |
| RE34,783 E | 11/1994 | Coates | 250/372 |
| 5,412,473 A | 5/1995 | Rosencwaig et al. | 356/451 |
| 5,486,701 A | 1/1996 | Norton et al. | 250/372 |
| 5,596,411 A | 1/1997 | Fanton et al. | 356/369 |
| 5,608,526 A | 3/1997 | Piwonka-Corle | 356/369 |
| 5,771,094 A | 6/1998 | Carter et al. | 356/326 |
| 5,798,837 A | 8/1998 | Aspnes et al. | 356/369 |
| 5,889,593 A | 3/1999 | Bareket et al. | 356/445 |
| 5,900,939 A | 5/1999 | Aspnes et al. | 356/369 |

(Continued)

OTHER PUBLICATIONS

PCT Publication WO 99/45340.

*Primary Examiner* — Roy M Punnoose
(74) *Attorney, Agent, or Firm* — James D. Welch

(57) ABSTRACT

System for, and method of ellipsometric investigation of and analysis of samples which have, for instance, a non-random effectively "regular" textured surface, and/or a surface characterized by an irregular array of faceted structures.

7 Claims, 8 Drawing Sheets

(56) References Cited

U.S. PATENT DOCUMENTS

| | | | |
|---|---|---|---|
| 5,910,842 A | 6/1999 | Piwonka-Corle | 356/369 |
| 5,963,327 A * | 10/1999 | He et al. | 356/369 |
| 6,091,499 A | 7/2000 | Abraham et al. | 356/375 |
| 6,600,560 B2 | 7/2003 | Mikkelsen et al. | 356/369 |
| 7,136,162 B1 * | 11/2006 | Liphardt et al. | 356/369 |
| 8,059,276 B2 * | 11/2011 | Hilfiker et al. | 356/369 |
| 8,248,607 B1 * | 8/2012 | Herzinger et al. | 356/369 |
| 2002/0024668 A1 | 2/2002 | Stehle et al. | |

* cited by examiner

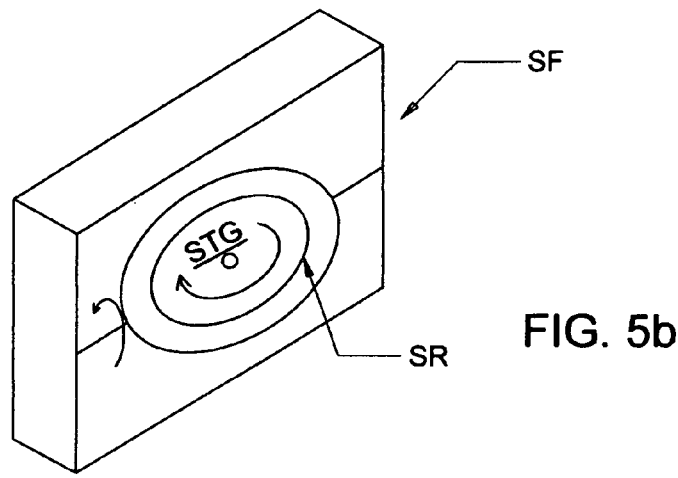
FIG. 5b
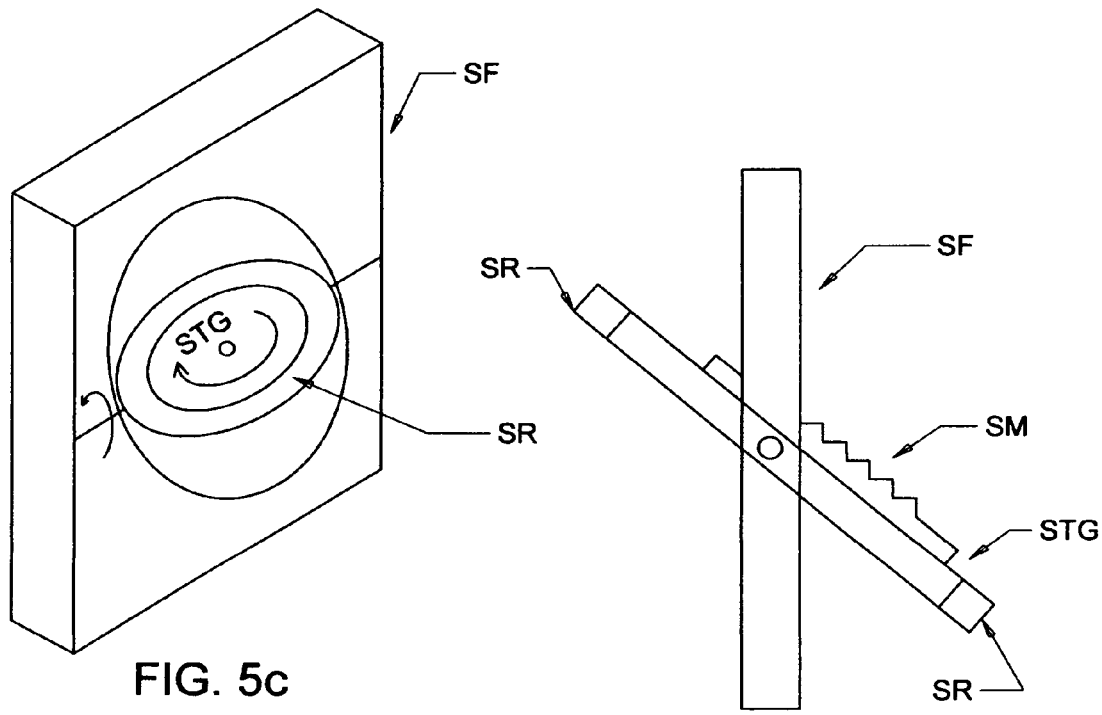
FIG. 5c
FIG. 5d

ELLIPSOMETRIC INVESTIGATION AND ANALYSIS OF TEXTURED SAMPLES

CROSS-REFERENCE TO EXISTING APPLICATIONS

This Application is a CIP of application Ser. No. 12/315,898 Filed Dec. 8, 2008 now U.S. Pat. No. 8,059,276 and therevia Claims Benefit of Provisional Application Ser. No. 61/126,233 filed May 2, 2008. This Application is a CIP of Pending application Ser. No. 12/075,956 Filed Mar. 14, 2008 now U.S. Pat. No. 7,830,512. Via the 898 Application this Application is also a CIP of application Ser. No. 11/980,262 Filed Oct. 30, 2007 now U.S. Pat. No. 7,619,752, which is a CIP of application Ser. No. 11/495,130 Filed Jul. 29, 2006 now U.S. Pat. No.7,333,198, and therevia this Application is a Divisional of patent application Ser. No. 11/177,207 Filed Jul. 8, 2005 now U.S. Pat. No. 7,084,978; and therevia a CIP of Ser. No. 10/652,696 Filed Sep. 2, 2003, (now U.S. Pat. No. 7,230,699); and therevia Claims Benefit of Provisional Application Ser. No. 60/459,690 Filed Apr. 3, 2003. This Application also, via the foregoing Applications, Claims Benefit of Provisional Application Ser. No. 60/588,315 Filed Jul. 15, 2004. This Application further is a CIP of application Ser. No. 11/145,470 Filed Jun. 6, 2005 now U.S. Pat. No. 7,327,456, and therevia this Application is a CIP of Ser. No. 10/376,677 Filed Feb. 28, 2003 (now U.S. Pat. No. 6,982,789), and therevia of Ser. No. 10/178,723 Filed Jun. 24, 2002, (now U.S. Pat. No. 6,950,182); Ser. No. 09/531,877 Filed Mar. 21, 2000; Ser. No. 09/583,229 Filed May 30, 2000, (now U.S. Pat. No. 6,804,004); Ser. No. 09/864,840 Filed May 24, 2001, (now U.S. Pat. No. 6,456,376); Ser. No. 10/943,821 Filed Sep. 17, 2004; Ser. No. 09/854,548 Filed May 14, 2001; and this Application Claims benefit of Provisional Application Ser. Nos. 60/300,714 Filed Jun. 26, 2001; 60/424,589 Filed Nov. 7, 2002; 60/427,043 Filed Nov. 18, 2002; 60/431,489 Filed Dec. 6, 2002.

To provide insight to priority it is disclosed that this Application is a CIP of Pending application Ser. No. 11/980,262 Filed Oct. 30, 2007, which is a CIP of Pending application Ser. No. 11/495,130 Filed Jul. 29, 2006, and therevia this Application is a Divisional of patent application Ser. No. 11/177,207 Filed Jul 8, 2005; and therevia a CIP of Ser. No. 10/652,696 Filed Sep. 2, 2003, (now U.S. Pat. No. 7,230,699); and therevia Claims Benefit of Provisional Application Ser. No. 60/459,690 Filed Apr. 3, 2003. This Application also, via the foregoing Applications, Claims Benefit of Provisional Application Ser. No. 60/588,315 Filed Jul. 15, 2004. This Application further is a CIP of application Ser. No. 11/145,470 Filed Jun. 6, 2005, and therevia this Application is a CIP of Ser. No. 10/376,677 Filed Feb. 28, 2003 (now U.S. Pat. No. 6,982,789), and therevia of Ser. No. 10/178,723 Filed Jun. 24, 2002, (now U.S. Pat. No. 6,950,182); Ser. No. 09/531,877 Filed Mar. 21, 2000; Ser. No. 09/583,229 Filed May 30, 2000, (now U.S. Pat. No. 6,804,004); Ser. No. 09/864,840 Filed May 24, 2001, (now U.S. Pat. No. 6,456,376); Ser. No. 10/943,821 Filed Sep. 17, 2004; Ser. No. 09/854,548 Filed May 14, 2001; and this Application Claims benefit of Provisional Application Serial Nos. 60/300,714 Filed Jun. 26, 01; 60/424,589 Filed Nov. 07, 2002; 60/427,043 Filed Nov. 18, 2002; 60/431,489 Filed Dec. 06, 2002.

It is noted that the most recent 262 Pending Application invention relates to systems for adjusting sample orientation, and more particularly to system and method for orienting the tilt and vertical position of samples in ellipsometer and the like systems. As mentioned above, it is known to place samples on stages in ellipsometer and the like systems, and to cause a polarized beam of electromagnetic radiation to impinge on said sample at an oblique angle thereto, interact with said sample and then enter a detector. It is also known that the "tilt" of a sample surface at a specific location thereon can affect realized angle and plane-of-incidence values actually achieved. Further, it is known to adjust the vertical height of the stage to position a sample such that a beam of electromagnetic radiation reflecting therefrom enters a detector. And, it is known to use a beam of electromagnetic radiation comprising a range of wavelengths, (eg. which can be smaller or larger than a facet feature on a sample to enable), investigation thereof).

TECHNICAL FIELD

The present invention relates to investigation of and analysis of samples using electromagnetic radiation, and more particularly to ellipsometric investigation of and analysis of samples which have, for instance, a non-random effectively "regular" textured surface and/or a surface characterized by an irregular array of faceted structures.

BACKGROUND

It is well known in the art to cause an electromagnetic beam to reflect from a sample, and by monitoring change in, for example, the intensity and/or polarization state of said beam resulting from interaction with the sample, determine properties of the sample, (eg. thickness of thin films on the sample surface, and optical constants). It is also known that where a sample surface reflects specularly essentially all incident electromagnetic radiation can be reflected from the sample into a detector and good data will typically be developed thereby. A problem can occur, however, where a sample has an irregular surface, as incident electromagnetic radiation becomes scattered by what amounts to the effects of said beam effectively approaching the sample surface at different angles and planes of incidence, at different locations thereon. When this occurs a large majority of the electromagnetic radiation which reflects from the sample surface is often directed other than into a detector, or is scattered, rather than specularly reflected thereinto, which scattered electromagnetic radiation causes problems in analysis of acquired data. The intensity of a collected portion of a reflected beam can then become too weak to be used in sample analysis and attempts to increase the intensity entering a detector, without consideration of from where on an irregular sample surface the additional collected electromagnetic radiation reflects, can lead to data which is noisy, depolarized, based on uncertain angles-of-incidence, and therefore can not be reliably analyzed to provide good results.

Existing Provisional and Utility Applications, (ie. 60/459,690 Filed Apr. 3, 2003 and Allowed application Ser. No. 10/652,696 Filed Sep. 2, 2003, now U.S. Pat. No. 7,230,699), by an Inventor herein, show a prior art system for detecting sample tilt, and a system which utilizes an ellipsometer beam reflected from a sample to perform vertical positioning of a stage. Importantly, FIG. 3b, therein, (presented as FIG. 3c herein), shows a sample which is very much the same as the textured faceted samples investigated by the present invention when rotated to a different orientation. The stage in said 699 Patent FIG. 3a, (presented as FIG. 3d herein), is shown as being rotatable in Angle-of-Incidence (AOI) Tip, Plane-of-Incidence (POI) Tilt and about a normal to the surface of the stage (STG), (and if present thereupon a specular sample). To point out differences between the 699 Patent system and the present invention, it is disclosed that the 669 Patent describes a beam splitter which is used to divert a portion of the reflected beam into a detector and used to mediate adjustment of the sample's vertical position and/or tilt. Said system does not secure relative position of the ellipsometer and sample, but provides for aligning a sample system and controlling the angle and plane-of-incidence at which a beam of electromagnetic radiation obliquely impinges on a monitored location of a surface of a sample, and comprises, as viewed in side elevation:

a sample supporting stage which can be translated in "X", "Y" or "Z" directions as well as rotated about "X", "Y" and optionally "Z" axes;

vertically above said stage there being a first beam splitter means, a lens and a first camera means for providing a view of a portion of the surface of said sample, said first beam splitter means optionally having positioned on a lower surface thereof light emitting means for providing light to the surface of said sample;

laterally with respect to said first beam splitter means there being a reflection means;

vertically above said reflection means there being a second beam splitter;

vertically above said second beam splitter there being a second camera means and laterally with respect to said second beam splitter, there being sequentially a lens and an essentially point source of electromagnetic radiation;

said first and second camera means each having associated therewith display means.

Said system further comprises an ellipsometer polarization state generator to cause, and a polarization stage detector to monitor, a beam of electromagnetic radiation which in use impinges on said monitored location on said surface of said sample at an oblique angle thereto.

In use said first camera means and its associated display means provide a view of at least a portion of the surface of a sample utilizing light provided by said light emitting means for providing light to the surface of said sample positioned on said lower surface of said first beam splitter, and said essentially point source of electromagnetic radiation provides electromagnetic radiation to the surface of said sample via said second beam splitter, said reflective means and said first beam splitter, and said sample supporting stage is caused to be translated in any of said "X", "Y" and "Z" directions as well as rotated about said "X", "Y" and optionally "Z" axes which are necessary to cause an interrogating beam of electromagnetic radiation provided by said essentially point source of a source of electromagnetic radiation to reflect from the surface of said sample, proceed back through said first beam splitter means, reflect from said reflective means, pass through said second beam splitter means, enter said second camera means and cause an image on the display means associated therewith which indicates that the monitored location on the sample surface is oriented so as to face substantially vertically.

The purpose of the foregoing is to align said sample surface to assure that said beam of electromagnetic radiation provided to said monitored location on the surface of said sample at an oblique angle approaches said surface at known intended angle-of-incidence and plane-of-incidence orientation, rather than at an angle-of-incidence and plane-of-incidence orientation which is modified by surface irregularities or non-flat samples.

Said system can further comprise a polarizer means in the path of said beam of electromagnetic radiation provided by said essentially point source of electromagnetic radiation, and in which said first beam splitter is sensitive to polarization state, and the polarizer means can be adjustable to enable control of the direction of polarization. The system point source of a source of electromagnetic radiation can comprise a fiber optic. The related Co-Pending 130 Application describes a related system.

Continuing, as it is relevant, Patent to Abraham et al., U.S. Pat. No. 6,091,499 is disclosed as it describes a method and system for automatic relative adjustment of samples in relation to an ellipsometer. Paraphrasing, said Abraham et al. system basically comprises:

a system for orienting a sample on a stage in an ellipsometer system comprising a first light source, a polarizer, said stage, an analyzer and a detector;

said system further comprising a detection system having a second light source, wherein said detection system is independently adjustable in relation to said ellipsometer, and wherein said detection system can be electronically locked into position relative to said ellipsometer so that said ellipsometer and said detection system can be adjusted as one unit in relationship to said stage, wherein said detection system can detect both a tilt of a sample placed onto said stage, and a distance of said sample from a coordinate source of the ellipsometer in two perpendicular axes; and said system further comprising an adjusting device, wherein said adjusting device can adjust tilt of said stage, and wherein said adjusting device can adjust the position of said ellipsometer and detection system when in an electronically locked relationship with respect to one another.

The 499 Patent drawings show a single source, (identified as (21)), provides, via beam splitters and reflection means, normal and oblique angle-of-incidence electromagnetic beams to a sample, which normal and oblique angle-of-incidence electromagnetic beams are each intercepted by a different detector, (identified as (24) and (25) respectively), after reflecting from the sample. The associated ellipsometer system comprises a separate source, (identified as (11)).

Additional known related Patents are:
Patent to Coates U.S. Pat. No. 4,373,817;
Patent to Coates U.S. Pat. No. 5,045,704;
RE. 34,783 to Coates;
Patent to Mikkelsen et al., U.S. Pat. No. 6,600,560;
Patent to Fanton et al., U.S. Pat. No. 5,596,411;
Patent to Piwonka-Corle et al., U.S. Pat. No. 5,910,842;
Patent to Piwonka-Corle et al., U.S. Pat. No. 5,608,526;
Patent to Bareket, U.S. Pat. No. 5,889,593;
Patent to Norton et al., U.S. Pat. No. 5,486,701;
Patent to Aspnes et al., U.S. Pat. No. 5,900,939;
Patent to Aspnes et al., U.S. Pat. No. 5,798,837;
Patent to Rosenscwaig et al., U.S. Pat. No. 5,412,473;
Patent to Carter et al., U.S. Pat. No. 5,771,094;
Patent to Liphardt, U.S. Pat. No. 7,136,162;
PCT Application Publication WO 99/45340;
Published Application of Stehle et al., No. US2002/0024668 A1.

Additionally, a recent computer search using the words "solar cell" and "sample tilt" provided no hits, while using the words "solar cell" and "substrate tilt" provided one hit each for Patents and Published Applications, (eg. U.S. Pat. No. 5,388,635 and Published Application US 2007/0267711), and using the words "solar cell" and "stage tilt" provided two hits each for Published Applications, (eg. US 2006/0048800 and 2004/0056779). None of these identified references are considered relevant.

Provisional Application Serial U.S. Pat. No. 61/126,233 filed May 02, 2008 in incorporated herein by reference.

Finally, while there is no known published disclosure thereof, Applicants have heard, "through the grapvine", that another entity (ie. Sentech), is using a large sample tilt technique similar to that disclosed herein, to facilitate investigation of solar cells. However, Applicants believe this alternative use is of very recent implementation and, for instance, does not involve use of spectroscopic electromagnetic radiation nor involve application of a sample stage rotation.

An approach to investigating a sample with a "regularly" textured surface, (ie. it comprises a surface having a repeated faceted pattern thereupon) and/or a surface characterized by an irregular array of faceted structures, would provide utility. If possible, such an approach would allow a researcher to collect an increased amount of "information containing" electromagnetic radiation which reflects from said sample textured surface and enters a detector to produce good data. It is such an approach that is subject of the present invention.

DISCLOSURE OF THE INVENTION

While the present invention is very much related to the sample orientation aspects of the inventions in above identified Parent Applications and Patents via CIP status, it is to be understood that said Parent Applications and Patents are primarily focused on aligning a sample to assure the Angle-of-Incidence (AOI) and Plane-of-Incidence (POI) of a beam of electromagnetic radiation which impinges on a specific identified location (a focused beam can be used), on a sample are known with precision so as to enable better analysis of data. That is, said Parent Applications and Patents are focused primarily on a method of aligning a sample via a tip/tilt action of a stage that supports the sample in a plane, optionally in combination with adjusting the position of the stage along a normal to said plane for each position on a sample which is investigated. Provision for rotating the stage about a normal thereto is also disclosed in the Parent Applications and Patents. Said approach is sequentially applied to samples with irregular surfaces at different locations thereupon. The present invention also involves adjusting the tip/tilt of a stage that supports the sample in a plane, but the focus thereof is modified to introducing a very significant stage tilt, (eg. demonstrated by FIG. 5d herein which shows a FIG. 5a stage (STG), optionally in combination with a Sample Rotation (SR) means, so that surface facets which are repeated in a textured sample surface (eg. see FIG. 3b in U.S. Pat. No. 7,230,699 and equivalent, FIG. 3c herein), are oriented to reflect electromagnetic radiation incident thereupon over a more significant area thereof, (eg. compare FIGS. 3b and 4a herein, with said FIG. 4a showing the preferred orientation), into a detector, while electromagnetic radiation incident on other locations of the textured sample are scattered away from the detector, (eg. see FIG. 3a herein). Where sample facet dimensions are more equal in orthogonal directions, (eg. see FIG. 4c herein), the 699 Patent FIG. 3b, (FIG. 3c herein), orientation capability can be used without rotation about a normal to the Stage (STG) Surface.

It is noted that typically, the incident beam of electromagnetic radiation used in practicing the present invention is not focused and its diameter is very large (eg. orders of magnitude larger), than are the facet dimensions of the surfaces which are repeated in a textured sample surface and which are to be oriented to reflect electromagnetic radiation incident thereupon into a detector. Further, the present invention can provide for collecting electromagnetic radiation reflected from the facets on the sample and focusing it into a detector.

For clarity, it is directly stated that the present invention retains the Parent Application's and Patent's focus of aligning a sample to assure the Angle-of-Incidence (AOI) and Plane-of-Incidence (POI) of a beam of electromagnetic radiation which impinges on a specific identified location, (a focused beam can be used), on a sample are known with precision so as to enable better analysis of data, but further introduces use of a significant sample tilt to orient sample facets as described above. That is, the present invention provides that the (AOI) and (POI) are accurately known at many locations on a textured sample, simultaneously.

It is mentioned that another approach to increasing the intensity of electromagnetic radiation reflected from a "rough" surface is to direct the beam to impinge on the rough surface at a large oblique AOI. This will result in an increased intensity entering a detector positioned to intercept the reflected beam, but a problem remains in that the data provided thereby typically contains so much noise, depolarized components and the like, that it can not be beneficially analyzed. While use of a very high AOI is within the scope of the present invention, the present invention teaches combining that with use of a very high tilt angle (again see FIG. 5d with reference to FIGS. 5a and 5b for Stage (STG) orientation capability). It is also disclosed that the optimum Stage Tilt angle is not necessarily what is computed from a known crystalline structure facet angle. For instance, (111) Silicon can be etched to provide facets which have an associated angle of 51.7 degrees. FIG. 4c herein provides insight to such a sample. It has been found in experimentation that an optimum stage calculated Tilt, (see FIG. 5d), for providing the greatest amount of reflected electromagnetic radiation into a detector is not necessarily that which exactly compensates this angle. In fact, the preferred embodiment of the present invention methodology provides for use of other than an optimum calculated Tilt.

Continuing, in view of the foregoing, it should be appreciated that where a surface of a sample has a non-random textured surface with some faceted regularly repeated pattern, it is possible to collect an increased amount of "information containing" electromagnetic radiation which reflects from said sample surface and enters a detector, by optimizing the orientation of the sample surface texturing. Such as a sample can be characterized as having the presence of a plurality of surface facet regions in planes which are substantially parallel to one another which can be simultaneously oriented. This is basically no different from the approach taught in Parent U.S. Pat. No. 7,230,699, except that in the present invention an electromagnetic beam diameter is intentionally significantly larger than facets being investigated so that many facets simultaneously reflect electromagnetic radiation into a detector.

The present invention comprises a method of analyzing physical and optical properties of a sample having first and second sides, one of which is textured, comprising:
  a) providing an ellipsometer or the like system comprising:
    a source of a spectroscopic beam of electromagnetic radiation;
    a polarizer;
    a stage system comprising:
      a stage frame oriented in a stage frame plane, and a stage; said stage being rotatably connected to said stage frame in a manner enabling tilting said stage with respect to said stage frame plane;
    an analyzer; and
    a detector.

Said spectroscopic ellipsometer can optionally further comprise at least one beam intensity controller selected from the group consisting of:

a means for controlling beam intensity between the source and detector;

a variable attenuator for controlling beam intensity between the source and detector;

a variable attenuator comprising two polarizers which can be adjusted with respect to one another to control the amount of electromagnetic radiation passing therethrough, between the source and detector;

a sequence of filters for controlling beam intensity between the source and detector; and said source of a spectroscopic beam of electromagnetic radiation is a plurality of sources for providing a plurality of beam intensities;

or the like.

Said method continues with the following steps:

b) positioning a sample having a textured surface onto said stage with the texture surface facing away from said stage;

c) causing a spectroscopic beam of electromagnetic radiation, provided by said source of a spectroscopic beam of electromagnetic radiation, to follow a beam locus and pass through said polarizer, impinge on and reflect from said textured sample surface at a location thereupon, pass through said analyzer and enter said detector, said beam of electromagnetic radiation also affected by the at least one selected beam intensity controller;

d) effecting a stage tilt to orient said textured sample surface in a plane oriented at between 10-90 degrees with respect to the plane of said stage frame;

e) collecting data provided by said detector; and f) analyzing collected detector data to determine physical and/or optical properties of said textured sample surface; and said method being characterized in that, at the location on said textured sample at which said beam of electromagnetic radiation impinges, there is identified a perpendicular to said surface, in which a plane-of-incidence is defined as a plane including both said spectroscopic beam locus and said perpendicular to said textured surface at said location whereat said beam impinges; and in which an angle-of-incidence is defined as that angle between said spectroscopic beam locus and said normal to said textured surface at said location whereat said beam impinges;

and said method comprises, while substantially maintaining said angle-of-incidence, causing the sample to tilt so that said perpendicular to said textured sample surface at the location on said textured sample at which said spectroscopic beam of electromagnetic radiation impinges is not in said defined plane-of-incidence, while data is collected in step e; and g) performing at least one selection from the group consisting of:

storing at least some data provided by said data detector in machine readable media;

analyzing at least some of the data provided by said data detector and storing at least some of the results of said analysis in machine readable media;

displaying at least some data provided by said data detector by electronic and/or non-electronic means;

analyzing at least some of the data provided by said data detector and displaying at least some of the results of said analysis by electronic and/or non-electronic means;

causing at least some data provided by said data detector to produce a signal which is applied to provide a concrete and tangible result; and analyzing at least some of the data provided by said data detector and causing at least some thereof to produce a signal which is applied to provide a concrete and tangible result.

Note, the range of 10-90 degrees is typical, but rotation can be effected between 0-90 degrees. Further, said range is to be interpreted to include 0 to negative (−90) degrees.

It is noted that at the location on said textured sample at which said spectroscopic beam of electromagnetic radiation impinges thereupon, there is identified a perpendicular to said surface, In which a plane-of-incidence is defined as that plane including both said spectroscopic beam locus and said perpendicular to said textured surface at said location whereat said beam impinges; and in which an angle-of-incidence is defined as that angle between the locus of said spectroscopic beam and said normal to said textured surface at said location whereat said beam impinges;

and said method can further comprise the step of causing the sample to tilt so that said perpendicular to said textured sample surface is not in said defined plane-of-incidence while data is collected in step e.

Said method can involve the sample plane-of-incidence tilt being set to a value at which said reflected beam reaching said detector is substantially optimized as defined by a selection from the group of:

wherein said electromagnetic beam is spectroscopic, the "quality" is enhanced, where quality is identified by data magnitude sensitivity to wavelength change; and the nature of the electromagnetic beam is enhanced as evidenced by the enabling of determination of at least one selection from the group of ellipsometric PSI and ellipsomtric DELTA therefrom.

Said method can involve the angle-of-incidence at which said beam approaches said textured sample being set to a value at which said reflected beam reaching said detector is substantially optimized as defined by a selection from the group of:

wherein said electromagnetic beam is spectroscopic, the "quality" is enhanced, where quality is identified by data magnitude sensitivity to wavelength change; and the nature of the electromagnetic beam is enhanced as evidenced by the enabling of determination of at least one selection from the group of ellipsometric PSI and ellipsomtric DELTA therefrom.

Said method can be characterized by at least one selection from the group consisting of:

a) a thin film is present on the surface of the textured sample which is in a tilted plane oriented at between 10-80 degrees with respect to the plane of said stage frame;

b) the surface of the textured sample is oriented in a tilted plane oriented at an angle with respect to the plane of said stage frame which is other than perpendicular to a plane-of-incidence including both said spectroscopic beam locus and a perpendicular to said textured surface at said location whereat said beam impinges;

c) the angle-of-incidence at which the beam of electromagnetic radiation impinges on a thin film present on said textured sample surface is between 10 and 80 degrees, and surface of the textured sample is in a tilted plane oriented at between 10-90 degrees with respect to the plane of said stage frame;

d) the surface of the textured sample is in a tilted plane oriented at between 0-90 degrees with respect to the plane of said stage frame and said textured sample is rotated about a normal to said tilted plane to optimize a signal which enters said detector, and said beam of electromagnetic radiation is spectroscopic;
e) said ellipsometer further comprises a means for increasing the intensity of the beam of electromagnetic radiation which impinges on and reflects from said surface of said textured sample surface;
f) said surface of said textured sample comprises facets from which electromagnetic radiation incident thereupon is reflected loci other than into said detector;
g) said surface of said textured samples comprise a non-random effectively "regular" textured surface and/or a surface characterized by an irregular array of faceted structures;
h) said surface of said textured sample comprises connector lines thereupon from which electromagnetic radiation incident thereupon is reflected other than into said detector;
i) said ellipsometer further comprises "X"-"Y" or R-THETA means for translating said stage and stage rotation means as a unit.

Another present invention method of analyzing physical and optical properties of a textured sample surface comprises:
a) providing an ellipsometer or the like system comprising:
  a source of a beam of electromagnetic radiation;
  a polarizer;
  a stage system comprising:
    a stage frame oriented in a stage frame plane;
    a stage rotation means; and
    a stage;
  said stage rotation means being rotatably connected to said stage frame in a manner enabling tilting said stage and stage rotation means, as a unit, with respect to said stage frame plane and said stage rotation means enabling rotation of said stage in a plane parallel to the surface of said stage;
  an analyzer; and
  a detector.

Said spectroscopic ellipsometer can optionally further comprise at least one beam intensity controller selected from the group consisting of:
  a means for controlling beam intensity between the source and detector;
  a variable attenuator for controlling beam intensity between the source and detector;
  a variable attenuator comprising two polarizers which can be adjusted with respect to one another to control the amount of electromagnetic radiation passing therethrough, between the source and detector;
  a sequence of filters for controlling beam intensity between the source and detector; and
  said source of a spectroscopic beam of electromagnetic radiation is a plurality of sources for providing a plurality of beam intensities;
or the like.

Said method continues with the steps:
b) positioning a sample having a textured surface onto said stage with the texture surface facing away from said stage;
c) causing a spectroscopic beam of electromagnetic radiation, provided by said source of a spectroscopic beam of electromagnetic radiation, to follow a beam locus and pass through said polarizer, impinge on and reflect from said textured sample surface at a location thereupon, pass through said analyzer and enter said detector, said beam of electromagnetic radiation also affected by the at least one selected beam intensity controller;
d) effecting a stage tilt to orient said textured sample surface in a plane oriented at between 10-90 degrees with respect to the plane of said stage frame;
e) collecting data provided by said detector; and
f) analyzing collected detector data to determine physical and/or optical properties of said textured sample surface;

said method being characterized in that, at the location on said textured sample at which said beam of electromagnetic radiation impinges, there is identified a perpendicular to said surface,
  in which a plane-of-incidence is defined as a plane including both said spectroscopic beam locus and said perpendicular to said textured surface at said location whereat said beam impinges; and
  in which an angle-of-incidence is defined as that angle between said spectroscopic beam locus and said normal to said textured surface at said location whereat said beam impinges;
and said method comprises, while substantially maintaining said angle-of-incidence, causing the sample to tilt so that said perpendicular to said textured sample surface at the location on said textured sample at which said spectroscopic beam of electromagnetic radiation impinges is not in said defined plane-of-incidence, while data is collected in step e.

In addition said method can include:
g) performing at least one selection from the group consisting of:
  storing at least some data provided by said data detector in machine readable media;
  analyzing at least some of the data provided by said data detector and storing at least some of the results of said analysis in machine readable media;
  displaying at least some data provided by said data detector by electronic and/or non-electronic means;
  analyzing at least some of the data provided by said data detector and displaying at least some of the results of said analysis by electronic and/or non-electronic means;
  causing at least some data provided by said data detector to produce a signal which is applied to provide a concrete and tangible result; and
  analyzing at least some of the data provided by said data detector and causing at least some thereof to produce a signal which is applied to provide a concrete and tangible result.

It is again noted that at the location on said textured sample at which said beam of electromagnetic radiation impinges thereupon, there is identified a perpendicular to said surface,
  in which a plane-of-incidence is defined as that plane including both said beam locus and said perpendicular to said textured surface at said location whereat said beam impinges; and
  in which an angle-of-incidence is defined as that angle between the locus of said beam and said normal to said textured surface at said location whereat said beam impinges;
and said method can further comprise the step of causing the sample to tilt so that said perpendicular to said textured sample surface is not in said defined plane-of-incidence while data is collected in step e.

Said method can involve the sample tilt being set to a value at which quality of said reflected beam reaching said detector is substantially optimized.

Said method can involve the angle-of-incidence at which said beam approaches said textured sample being set to a value at which quality of said reflected beam reaching said detector is substantially optimized.

Said method can involve the stage rotation means being applied to cause said stage to rotate in a plane substantially parallel to said textured sample surface to a position at which quality of said reflected beam reaching said detector is substantially optimized.

Said method can involve, in the step a) providing an ellipsometer or the like system which further comprises providing a means for controlling the intensity of the spectroscopic beam per se. that enters the detector. Though not limiting, said means for controlling the intensity of the spectroscopic beam per se. can comprise a selection from the group consisting of:
- rotatable crossed polarizers placed into said beam;
- a series of different opaque filters which can be sequentially inserted into said beam;
- a series of different intensity sources.

While not a primary focus of the present invention, it is mentioned that, as disclosed in application Ser. No. 12/075,956, the rotatable crossed polarizer approach can control beam intensity as a function of wavelength, where a source thereof provides a polychromatic beam. A sequence of crossed polarizers can involve the second thereof being a beam polarizer in an ellipsometer or polarimeter system, which provides a set beam polarization state to a substrate. When the first of said crossed polarizers is rotated with respect thereto, the intensity exiting the second thereof is, substantially uniformly, controlled over the entire range of wavelengths. The crossed polarizer system can, however, further comprise a compensator placed in between the first and second of the crossed polarizers, and said compensator serves to provide selective attenuation of some wavelengths more than others. It is to be understood that the compensator just mentioned is not that involved in configuring a rotation compensator ellipsometer system. In a rotation compensator ellipsometer system an additional compensator is placed between the second crossed polarizer and an analyzer which is positioned before a detector, and it is that additional compensator which is caused to rotate during data acquisition. This is not to be considered, however, as limiting application of the present invention to being implemented with only rotating compensator systems. It is specifically disclosed that the present invention can be practiced using any type of ellipsometer or polarimeter system. In particular, this includes rotating polarizer, rotation analyzer and phase modulation systems. Further, where a compensator is applied it can be of Berek-type, where the optical axis is perpendicular to a surface thereof into which a beam is entered, and where a "tipping" of said Berek-type compensator is used to affect a phase angle between orthogonal components of a polarized beam passed therethrough, or it can be of a conventional-type where the optical axis is parallel to a surface thereof into which a beam is entered, and where a "rotation" of said conventional-type compensator is used to affect a phase angle between orthogonal components of a polarized beam passed therethrough.

Said method can involve an ellipsometer/sample combination characterized by at least one selection from the group:
a) a thin film is present on the surface of the textured sample which is in a tilted plane oriented at between 10-80 degrees with respect to the plane of said stage frame;
b) the surface of the textured sample is oriented in a tilted plane oriented at an angle with respect to the plane of said stage frame which is other than perpendicular to a plane-of-incidence including both said spectroscopic beam locus and a perpendicular to said textured surface at said location whereat said beam impinges;
c) the angle-of-incidence at which the beam of electromagnetic radiation impinges on a thin film present on said textured sample surface is between 10 and 80 degrees, and surface of the textured sample is in a tilted plane oriented at between 10-90 degrees with respect to the plane of said stage frame;
d) the surface of the textured sample is in a tilted plane oriented at between 0-90 degrees with respect to the plane of said stage frame and said textured sample is rotated about a normal to said tilted plane to optimize a signal which enters said detector, and said beam of electromagnetic radiation is spectroscopic;
e) said ellipsometer further comprises a means for increasing the intensity of the beam of electromagnetic radiation which impinges on and reflects from said surface of said textured sample surface;
f) said surface of said textured sample comprises facets from which electromagnetic radiation incident thereupon is reflected other than into said detector;
g) said surface of said textured samples comprise a non-random effectively "regular" textured surface and/or a surface characterized by an irregular array of faceted structures;
h) said surface of said textured sample comprises connector lines thereupon from which electromagnetic radiation incident thereupon is reflected other than into said detector;
i) said ellipsometer further comprises "X"-"Y" or R-THETA means for translating said stage and stage rotation means as a unit.

The present invention can be practiced using a spectroscopic ellipsometer which comprises:
- a spectroscopic source of a beam of electromagnetic radiation;
- a polarizer;
- a stage system comprising:
  - a stage frame oriented in a stage frame plane;
  - a stage rotation means; and
  - a stage;
  - said stage rotation means being rotatably connected to said stage frame in a manner enabling tilting said stage and stage rotation means, as a unit, with respect to said stage frame plane and said stage rotation means enabling rotation of said stage in a plane parallel to the surface of said stage;
- an analyzer; and
- a detector;

said spectroscopic ellipsometer, while being applied to obtain ellipsometric data, being arranged such that said spectroscopic source of a beam of electromagnetic radiation provides a spectroscopic beam which is caused to pass through said polarizer, reflect from a sample on said stage system when it is arranged to tilt said stage and stage rotation means, as a unit, with respect to said stage frame plane so that a plane including including both incident and reflected spectroscopic beams, does not include a perpendicular to the surface of said sample at the point of interaction therewith, then pass through said analyzer and enter said detector, said spectroscopic beam of electromagnetic radiation also being affected by said at least one selected beam intensity controller selected from the group consisting of:
- a means for controlling beam intensity between the source and detector;
- a variable attenuator for controlling beam intensity between the source and detector;
- a variable attenuator comprising two polarizers which can be adjusted with respect to one another to control the amount of electromagnetic radiation passing therethrough, between the source and detector;

a sequence of filters for controlling beam intensity between the source and detector; and said source of a spectroscopic beam of electromagnetic radiation is a plurality of sources for providing a plurality of beam intensities;

or the like.

Said system can further comprise at least one compensator between the polarizer and analyzer positioned so that the beam of electromagnetic radiation provided by said spectroscopic source of a beam of electromagnetic radiation, which interacts with said textured sample, passes therethrough, and causing said at least one compensator to rotate substantially about the locus of said beam of electromagnetic radiation during the step of obtaining ellipsometric data over a spectroscopic range of wavelengths.

Another present invention method of improving results achieved by investigating a sample with a textured surface with electromagnetic radiation comprises:

a) providing a spectroscopic ellipsometer as described above;

b) placing a sample with a specularly reflecting surface on said stage;

c) while causing said a spectroscopic source of a beam of electromagnetic radiation to direct a spectroscopic beam of electromagnetic radiation to pass through said a variable attenuator and polarizer, toward said specular surface of said sample with a specularly reflecting surface, in coordination, adjusting the angle-of-incidence of said spectroscopic beam of electromagnetic radiation with respect to said sample, and the orientation of said sample by adjustment of said stage rotation means adjusting the orientation of said stage and stage rotation means, as a unit, with respect to said stage frame plane, and optionally adjusting said stage rotation to orient the surface of said sample a plane parallel to the surface of said stage, so that the electromagnetic radiation reflected from said sample passes through said analyzer and enters said detector;

d) adjusting said variable attenuator so that the intensity of the reflected electromagnetic radiation entering said detector does not saturate said detector;

e) removing said sample with a specular surface from said stage and placing a sample with a textured surface thereupon in its place;

f) in coordination adjusting the variable attenuator, and the orientation of said textured sample surface by adjustment of said stage rotation means, and tilting said stage and stage rotation means as a unit, with respect to said stage frame plane so that the electromagnetic radiation reflected from said sample with a textured surface passes through said analyzer and enters said detector;

g) obtaining ellipsometric data over a spectroscopic range of wavelengths;

h) analyzing said ellipsometric data to evaluate optical and physical properties of said textured sample.

Said method can further include providing at least one compensator between the polarizer and analyzer positioned so that the beam of electromagnetic radiation provided by said spectroscopic source of a beam of electromagnetic radiation, which interacts with said textured sample, passes therethrough, and causing said at least one compensator to rotate substantially about the locus of said beam of electromagnetic radiation during the step of obtaining ellipsometric data over a spectroscopic range of wavelengths. In the alternative said polarizer and/or analyzer can caused to rotate during data acquisition.

Said method can involve investigating a sample with a textured surface characterized by the presence of a plurality of facet surfaces which are substantially parallel to one another, and the step of adjusting said stage rotation means, and titling said stage and stage rotation means as a unit, with respect to said stage frame plane, so that the electromagnetic radiation reflected from said sample with a textured surface passes through said analyzer and enters said detector involves effecting orientation of said sample so that electromagnetic radiation reflecting from said plurality of facet surfaces which are substantially parallel to one another enters said detector, which substantially all electromagnetic radiation which does not reflect from said plurality of facet surfaces which are substantially parallel to one another does not so enter said detector. The preferred system for providing this capability is better discussed later in this Section of this Specification.

Said method can involve investigation of the textured surface of said sample is coated with a thin film, and the steps of obtaining ellipsometric data over a spectroscopic range of wavelengths and analyzing said ellipsometric data to evaluate physical and optical properties of said textured sample can involve determining physical and optical properties of said thin film. For instance, a present invention method can involve analyzing physical and optical properties of a thin film on a textured sample front side surface, where said sample has a similarly textured backside without the thin film being present thereupon, or a region on the front side that has no thin film present, or a different but essentially similar sample that has a region without a thin film present thereupon can even be applied. As alluded to before, said sample texturing is characterized as a non-random effectively "regular" textured surface and/or a surface characterized by an irregular array of faceted structures. Said method comprises the steps of:

a) obtaining ellipsometric data for both said sample with, and without a thin film present, (eg. from both the front and back sides of said sample by taking data from one side and then flipping the sample over and again acquiring data, or from regions comprising and not comprising a thin film on the one side thereof or by obtaining data from different but essentially similar samples which in combination provide both film present and absent regions);

b) proposing a mathematical/optical model for the sample without a thin film present, and a mathematical/optical model for the sample front side which has a thin film present;

c) fitting said ellipsometric data obtained from the sample without a thin film present to said mathematical/optical model for said sample without a thin film present to obtain values for sample per se. physical and optical properties, such as effective media surface roughness and/or void percentage;

d) while holding values for the sample per se. physical and optical properties determined in step c, fitting said ellipsometric data obtained from the side of said sample having a thin film present to said mathematical/optical model for said side having a thin film present to obtain values for said thin film physical and optical properties.

Another method of analyzing physical and optical properties of a thin film on a textured sample front side surface comprises:

a) providing an ellipsometer or the like system comprising:

a source of a beam of electromagnetic radiation;

a polarizer;

a stage system comprising:

a stage frame oriented in a stage frame plane;

a stage rotation means; and
a stage;
said stage rotation means being rotatably connected to said stage frame in a manner enabling tilting said stage and stage rotation means, as a unit, with respect to said stage frame plane and said stage rotation means enabling rotation of said stage in a plane parallel to the surface of said stage;
an analyzer; and
a detector.

Said spectroscopic ellipsometer can optionally further comprise at least one beam intensity controller selected from the group consisting of:
  a means for controlling beam intensity between the source and detector;
  a variable attenuator for controlling beam intensity between the source and detector;
  a variable attenuator comprising two polarizers which can be adjusted with respect to one another to control the amount of electromagnetic radiation passing therethrough, between the source and detector;
  a sequence of filters for controlling beam intensity between the source and detector; and
  said source of a spectroscopic beam of electromagnetic radiation is a plurality of sources for providing a plurality of beam intensities.

Said method then further comprises:
  b) positioning a textured sample onto said stage with the thin film on surface of said textured sample facing away from said stage;
  c) causing a beam of electromagnetic radiation, provided by said source of a beam of electromagnetic radiation, to pass through said polarizer, impinge on and reflect from said textured sample, pass through said analyzer and enter said detector, said beam of electromagnetic radiation optionally being affected by the at least one selected beam intensity controller if it is present;
  d) effecting a stage and stage rotation means tilt to orient said textured sample surface having a thin film thereupon in a plane oriented at, for instance, between 10-80 degrees with respect to the plane of said stage frame;
  e) while monitoring detector data output, causing said stage rotation means to rotate the textured sample in the plane parallel to the surface of said stage until said data output is of a sufficient quality to allow beneficial analysis thereof;
  f) optionally repeating steps d and e using different stage and stage rotation means tilts to orient said textured sample front surface having a thin film thereupon in a different plane oriented at between 10-90 degrees with respect to the plane of said stage frame, until a best combination of stage and stage rotation means tilt, and stage rotation in the plane parallel to the surface of said stage is determined based on data output is of a nature to allow beneficial analysis thereof, as evidenced by the enabling of determination of at least one selection from the group of ellipsometric PSI and ellipsomtric DELTA therefrom;
  g) analyzing detector data collected to determine physical and/or optical properties of said thin film on said textured sample front side surface.

Said method can further comprise placing said textured sample onto said stage with the thin film on surface of said textured sample facing toward said stage and causing a beam of electromagnetic radiation, provided by said source of a beam of electromagnetic radiation, to pass through said polarizer, impinge on and reflect from said backside of said textured sample, pass through said analyzer and enter said detector, followed by analyzing data provided by said detector to evaluate parameters corresponding to the non-thin film substrate component of said textured sample, and using the results in the procedure to better evaluate the physical and optical properties of the thin film. As mentioned above, a region on the sample front side that has no thin film present, or a different but essentially similar sample that has a region without a thin film present thereupon can even be applied instead of data acquired by investigating the back side.

This can include said method further comprising:
  h) positioning a textured sample onto said stage with the thin film on said front surface of said sample facing toward said stage;
  i) causing a beam of electromagnetic radiation, provided by said source of a beam of electromagnetic radiation, to pass through said polarizer, impinge on and reflect from said sample as so positioned, pass through said analyzer and enter said detector, said beam of electromagnetic radiation also affected by the at least one selected beam intensity controller;
  J) effecting a stage and stage rotation means tilt to orient said sample surface facing away from said stage in a plane oriented at, for instance, between 10-80 degrees with respect to the plane of said stage frame;
  k) while monitoring detector data output, causing said stage rotation means to rotate the textured sample in the plane parallel to the surface of said stage until said data output is of a sufficient quality to allow beneficial analysis thereof;
  l) optionally repeating steps i and j using different stage and stage rotation means tilts to orient said sample surface facing away from said stage as oriented in a different plane oriented at between 10-90 degrees with respect to the plane of said stage frame, until a best combination of stage and stage rotation means tilt, and stage rotation in the plane parallel to the surface of said stage is determined based on data output is of a nature to allow beneficial analysis thereof, as evidenced by the enabling of determination of at least one selection from the group of ellipsometric PSI and ellipsomtric DELTA therefrom;
  m) obtaining data from said detector;
  n) simultaneously analyzing detector data collected from the sample when the textured surface is facing away from, and collected from the sample when the textured surface is facing toward said stage, to determine physical and/or optical properties of said thin film on said textured sample front side surface.

(Note, in steps h-n instead of accessing the backside of a sample, a region on the frontside that does not have a thin film present can be substituted and the method remain the same otherwise).

The foregoing method can also be characterized by at least one selection from the group consisting of:
  a) the thin film on the surface of the textured sample is in a tilted plane oriented at, for instance, between 10-80 degrees with respect to the plane of said stage frame, and said beam of electromagnetic radiation is spectroscopic;
  b) the thin film on the surface of the textured sample is oriented in a tilted plane oriented at an angle with respect to the plane of said stage frame which is other than what the angle of facets on the textured sample would indicate as optimum, and said beam of electromagnetic radiation is spectroscopic;
  c) the angle-of-incidence at which the beam of electromagnetic radiation impinges on said thin film on said textured sample surface is between 10 and 80 degrees, and the thin film on the surface of the textured sample is in a tilted plane oriented at between 10-90 degrees with respect to the plane of said stage frame, and said beam of electromagnetic radiation is spectroscopic;

d) the thin film on the surface of the textured sample is in a tilted plane oriented at between 0-90 degrees with respect to the plane of said stage frame and said textured sample is rotated about a normal to said tilted plane to optimize a signal which enters said detector, and said beam of electromagnetic radiation is spectroscopic;

e) said ellipsometer further comprises a means for increasing the intensity of the beam of electromagnetic radiation which impinges on and reflects from said surface of said textured sample surface;

f) said surface of said textured sample comprises facets from which electromagnetic radiation incident thereupon is reflected other than into said detector;

g) said surface of said textured samples comprise a nonrandom effectively "regular" textured surface, and/or a surface characterized by an irregular array of faceted structures;

h) said surface of said textured sample comprises connector lines thereupon from which electromagnetic radiation incident thereupon is reflected other than into said detector;

i) said ellipsometer further comprises "X"-"Y" or R-THETA means for translating said stage and stage rotation means as a unit.

As regards h) above, for clarity it is further noted that where the surface of said textured sample comprises connector lines thereupon, (eg. current collecting traces on a solar cell), they do not lie in the same plane as do, for instance, facet surfaces. It should be apparent that if the sample is titled so that electromagnetic radiation incident thereupon reflects into a detector from facet surfaces, then electromagnetic radiation which reflects from the connector lines will reflect in a plane other than appropriate to direct it into said detector.

In the foregoing method, it is also disclosed that it is further possible to simultaneously analyze data obtained at a plurality of stage tip, tilt and rotation settings.

Another method can analyze physical and optical properties of a backside of a sample having front and back side surfaces, comprising:
a) providing an ellipsometer or the like system comprising:
  a source of a beam of electromagnetic radiation;
  a polarizer;
  a stage system comprising:
    a stage frame oriented in a stage frame plane;
    a stage rotation means; and
    a stage;
    said stage rotation means being rotatably connected to said stage frame in a manner enabling tilting said stage and stage rotation means as a unit, with respect to said stage frame plane, and said stage rotation means enabling rotation of said stage in a plane parallel to the surface of said stage;
  an analyzer; and
  a detector;
said ellipsometer optionally further comprising at least one beam intensity controller selected from the group consisting of:
  a means for controlling beam intensity between the source and detector;
  a variable attenuator for controlling beam intensity between the source and detector;
  a variable attenuator comprising two polarizers which can be adjusted with respect to one another to control the amount of electromagnetic radiation passing therethrough;
  a sequence of filters for controlling beam intensity between the source and detector; and
  said source of a beam of electromagnetic radiation is a plurality of sources for providing a plurality of beam intensities.

Said method continues with:
b) positioning a sample characterized by a selection from the group consisting of having:
  a smooth; and
  a textured;
backside onto said stage with the back surface of said sample facing away from said stage;
c) causing a beam of electromagnetic radiation, provided by said source of a beam of electromagnetic radiation, to pass through said polarizer, impinge on and reflect from said back side of said sample, pass through said analyzer and enter said detector, said beam of electromagnetic radiation also being affected by said at least one selected beam intensity controller;
d) effecting a stage and stage rotation means tilt to orient said back side of said sample in a plane oriented at between 0-90 degrees with respect to the plane of said stage frame;
e) while monitoring detector data output, causing said stage rotation means to rotate the sample in the plane parallel to the surface of said stage until said data output is of a nature to allow beneficial analysis thereof, as evidenced by the enabling of determination of at least one selection from the group of ellipsometric PSI and ellipsomtric DELTA therefrom.

Said method can also comprise:
f) optionally repeating steps d and e using different stage and stage rotation means tilts to orient said back sample surface in a different plane oriented at between 10-90 degrees with respect to the plane of said stage frame, until a best combination of stage and stage rotation means tilt, and stage rotation in the plane parallel to the surface of said stage is determined based on data output being of a nature to allow beneficial analysis thereof, as evidenced by the enabling of determination of at least one selection from the group of ellipsometric PSI and ellipsomtric DELTA therefrom;
g) analyzing detector data collected to determine physical and/or optical properties of said backside textured sample backside surface.

Said method can involve said sample having a textured frontside with a thin film on the surface thereof and in which said method further comprises placing said sample onto said stage with the thin film on surface of said textured sample facing away from said stage and causing a beam of electromagnetic radiation, provided by said source of a beam of electromagnetic radiation, to pass through said polarizer, impinge on and reflect from said frontside of said textured sample, pass through said analyzer and enter said detector, followed by analyzing data provided by said detector to evaluate parameters corresponding to the thin film substrate component of said textured sample, in combination with use of using the results from steps a-g in the procedure to aide with evaluating the physical and optical properties of the thin film on the frontside textured surface.

Another method of improving results achieved by investigating a sample having a textured, or an irregular array of faceted structures on a surface thereof with electromagnetic radiation, involving orientating a monitored location on said sample, said method comprises the steps of:
  a) providing a stage for supporting a sample, said stage having means for effecting rotation about said "X" or "Y", and "Z" axes, Another method of improving results achieved by investigating a sample having a textured, or an irregular array of faceted structures on a surface thereof with electromagnetic radiation, involving orientating a monitored location on said sample, said method comprises the steps of:
  a) providing a stage for supporting a sample, said stage having means for effecting rotation about said "X" or "Y", and "Z" axes, wherein said "Z" axis is substantially perpendicular to said surface having a textured surface or an irregular array of faceted structures;
  b) placing a sample with a textured surface or an irregular array of faceted structures onto said stage with the textured surface or an irregular array of faceted structures facing away from said stage;
  c) causing a beam of electromagnetic radiation to impinge on a monitored location on said textured surface or irregular array of faceted structures and enter a detector;
  d) rotating said sample about the "X" and/or "Y" axis and about said "Z" axis while monitoring detector output to identify sample orientation that enables acquisition of data that is characterized by at least one selection selection from the group of:
    where the electromagnetic beam is spectroscopic, a quality to allow beneficial analysis thereof, wherein "quality" is identified by data magnitude sensitivity to wavelength change; and
    of a nature to allow beneficial analysis thereof, as evidenced by the enabling of determination of at least one selection from the group of ellipsometric PSI and ellipsomtric DELTA therefrom.

Said method can provide that the sample is tilted so that a plane including including both incident and reflected spectroscopic beams, does not include a perpendicular to the surface of said sample at the point of interaction therewith.

It is noted that any of the methods disclosed herein can further include performing at least one selection from the group consisting of:
  storing at least some data provided by said data detector in machine readable media;
  analyzing at least some of the data provided by said data detector and storing at least some of the results of said analysis in machine readable media;
  displaying at least some data provided by said data detector by electronic and/or non-electronic means;
  analyzing at least some of the data provided by said data detector and displaying at least some of the results of said analysis by electronic and/or non-electronic means;
  causing at least some data provided by said data detector to produce a signal which is applied to provide a concrete and tangible result; and
  analyzing at least some of the data provided by said data detector and causing at least some thereof to produce a signal which is applied to provide a concrete and tangible result.

For additional insight, as an important capability of the Present Invention System is control of beam intensity, the preferred present invention system adds a control polarizer, and optionally a sequentially located control compensator, between the source of a beam of electromagnetic radiation and the beam polarizer in ellipsometer or polarimeter system, such that a beam of electromagnetic radiation provided by the source thereof passes through the control polarizer and optionally, when present, the control compensator, then through the beam polarizer and impinge on a sample, interact therewith, (eg. typically reflect therefrom but possibly transmit therethrough), and then pass through the analyzer and into the detector. Again, the control polarizer is positioned before the beam polarizer and in use is rotated with respect to the beam polarizer to substantially uniformly attenuate the intensity of all wavelengths which pass through said beam polarizer. And again, the present invention can also position a control compensator between the control and beam polarizers, which control compensator can be applied to cause selective attenuation of some wavelengths in the spectrum more than others. In use the beam polarizer is caused to set a polarization state in a beam exiting therefrom, and the control polarizer is rotated with respect to said beam polarizer to substantially uniformly control the intensity of the beam exiting the beam polarizer over a spectrum of wavelengths. The system can further comprise adjustment of a compensator between said control and beam polarizers which serves to cause selective attenuation of some wavelengths more than others in said spectrum of wavelengths. (It is noted that where a Berek-type control compensator, which has its optical axis perpendicular to a surface thereof which a beam enters is used, the terminology "rotation" thereof should be interpreted to mean a tipping thereof to position the optical axis other than parallel to the locus of the beam which passes therethrough, and where the control compensator has its optical axis in the plane of a surface thereof which a beam enters is used, rotation should be interpreted to means an actual rotation about a perpendicular to said surface).

A method of controlling the intensity of a beam of electromagnetic radiation over a spectral range, comprises the steps of:
  a) providing a system for controlling the intensity of a beam of electromagnetic radiation as described above;
  b) setting a beam polarization state with the beam polarizer and rotating the control polarizer with respect thereto to control the intensity.

Said method can further comprise providing a compensator between said control and beam polarizers which serves to selectively attenuate the intensity of some wavelengths in said spectrum more than others.

A typical procedure provides that the control and beam polarizers be rotated with respect to one another so that less intensity than is possible from the source, proceeds to the sample. This might be approached using a highly reflective test sample, for instance and the control polarizer adjusted to provide a non-saturating signal to the detector. When a less reflective sample is investigated, the control and beam polarizers can then be rotated with respect to one another so that greater intensity is applied to the less reflective sample. When present, the control compensator can be also be adjusted to further control the intensity vs. wavelength characteristic of a beam impinging on the sample.

For clarity, it is recited that the present invention can comprise an ellipsometer or polarimeter system comprising means for controlling the intensity of a beam of electromagnetic radiation as a function of wavelength comprising:
  a source of a polychromatic beam of electromagnetic radiation;
  a sequence of a control polarizer, a control compensator and beam polarizer;
  said control and beam polarizers and said control compensator being rotatable with respect to one another,
  said system further comprising:
    an analyzer; and
    a detector;

such that in use the polarized beam provided by said source which exits said beam polarizer, interacts with a sample and then passes through said analyzer and into said detector; such that in use the beam polarizer is caused to set a polarization state in a beam exiting therefrom, and the control polarizer and control compensator can be rotated with respect to said beam polarizer to substantially uniformly control the intensity of the beam exiting the beam polarizer over a spectrum of wavelengths.

Said ellipsometer or polarimeter system can further comprise at least one system compensator between said beam polarizer and said analyzer.

The present invention also comprises a method of controlling the intensity of a beam of electromagnetic radiation over a spectral range, comprising the steps of:

a) providing an ellipsometer or polarimeter system as described just above;

b) setting a beam polarization state with the beam polarizer and rotating the control polarizer and/or control compensator with respect thereto to control the intensity of said beam over the spectrum of wavelengths.

The present invention will be better understood by reference to the Detailed Description Section of this Disclosure, in conjunction with the Drawings.

BRIEF DESCRIPTION OF THE DRAWINGS

FIGS. 4b1 and 4b2 show top and side views of a textured sample which comprises a surface with a multiplicity of faceted pyramid shaped structures, with FIG. 4b2 indicating facet texturing can be present on front and back of a sample.

FIG. 4b3 shows that the sample of FIG. 4b2 can have a thin film a front side thereof.

FIG. 5b shows how the vertically oriented stage of FIG. 5a comprises a stage frame, a stage rotation effecting means, and the stage per se.

FIG. 5c shows a perspective view of how the stage rotation effecting means and the stage per se. of FIGS. 5a and 5b can be rotated in the stage frame, FIG. 5d shows a side view of the system in FIG. 5c, with a sample mounted to the stage per se.

DETAILED DESCRIPTION

Figure 1:
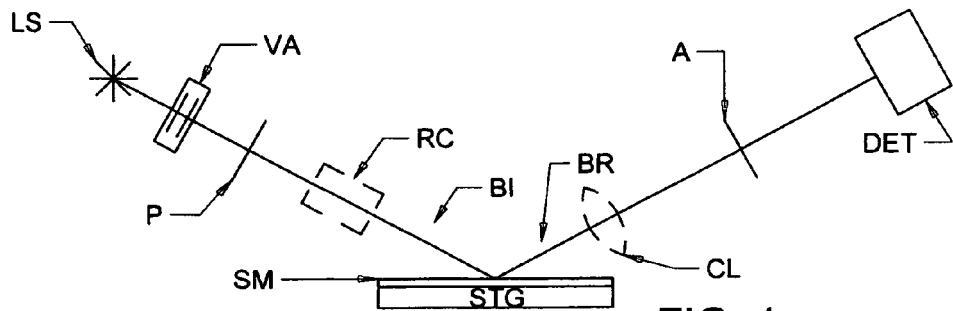
FIG. 1 shows a demonstrative ellipsometer system.

Turning now to the Drawings, FIG. 1 shows a basic well known demonstrative ellipsometer system comprising a Spectroscopic Source (LS) of a beam of electromagnetic radiation, a Variable Attenuator (VA), an optional Rotating Compensator, a Sample (SM) Stage (STG), an optional Collecting Means (CL), and Analyzer (A) and a Detector (DET). It is noted that the Variable Attenuator (VA) can be comprised of two polarizers which can be adjusted with respect to one another to control the intensity of electromagnetic radiation which passes therethrough.

Figure 2:
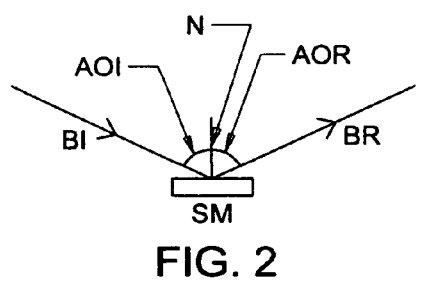
FIG. 2 shows an incident beam of electromagnetic radiation reflecting from a sample with a specular surface.

Continuing, FIGS. 1 and 2 show an Incident Beam (BI) of electromagnetic radiation reflecting as Reflected Beam (BR) from a Sample (SM) with a specular surface. Note that the Normal to the surface provides a reference for identifying Angle-of-Incidence (AOI) and Angle-of-Reflection (AOR). Note that a Plane-of-Incidence is defined as including both the locus of the Incident Beam (BI) and said Normal (N).

Figure 3A:
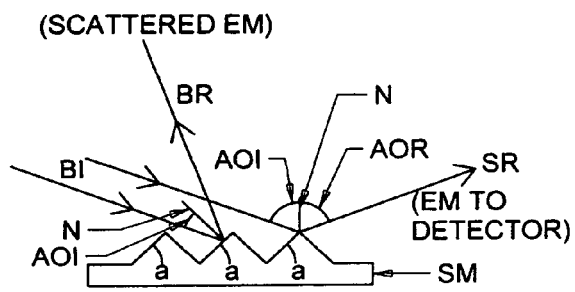
FIG. 3a is shows an incident beam of electromagnetic radiation reflecting from a sample with an irregular surface.
Figure 4A:
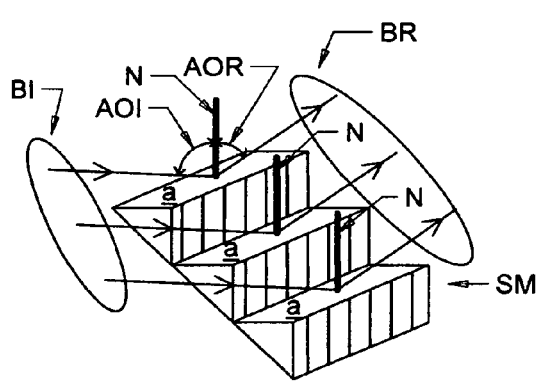
FIG. 4a showing the preferred textured sample orientation.
Figure 3B:
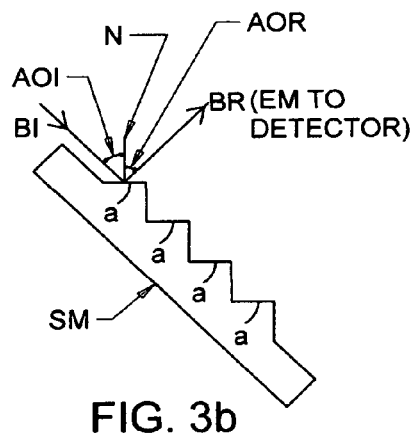
FIG. 3b shows a sample with an irregular surface oriented to increase the amount of electromagnetic radiation reflected therefrom toward a detector.
Figure 4C:
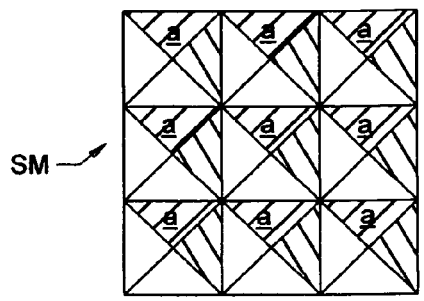
FIG. 4c shows how orienting the sample shown in FIGS. 4b1 and 4b2 much as the sample of FIGS. 3a and 3b is oriented in FIG. 4a1 can lead to increased reflected electromagnetic radiation reflected therefrom toward a detector.
Figure 4C:
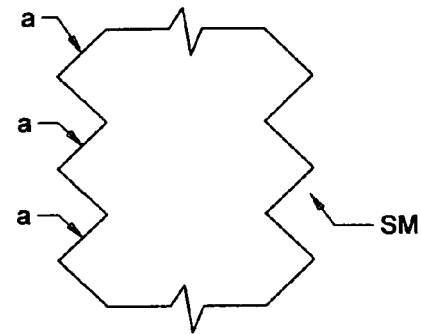
Figure 4C:
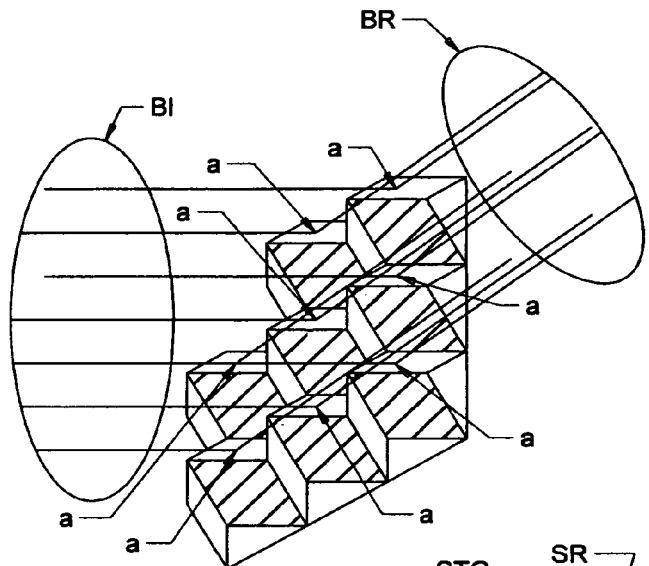

FIG. 3a shows an Incident Beam (BI) of electromagnetic radiation reflecting from a Sample (SM) with an irregular surface. Said FIG. 3a shows how the Normal (N) to the Sample (SM) surface varies in direction with position on said Sample (SM), such that electromagnetic radiation reflected at various locations proceed along different loci. Note that only a small amount of reflected electromagnetic radiation, from the peaks of the shown texture pattern, proceeds toward a Detector. This can lead to far to low an intensity entering the Detector to be analyzed. FIG. 3b shows how re-orienting the Sample (SM) in FIG. 3a can increase the amount of electromagnetic radiation reflected from facet (a) toward a Detector (DET) by presenting the breadth of -a- facet (a) to so direct reflected electromagnetic radiation. FIG. 4a shows how further re-orienting the Sample (SM) of FIG. 3b can greatly increase the amount of electromagnetic radiation reflected therefrom toward a Detector (DET) by positioning a plurality of facets (a) as shown to reflect electromagnetic radiation toward said Detector (DET). Note that the planes of the facets (a) in FIGS. 4a and 4c are substantially parallel to one another. This is important as electromagnetic radiation can simultaneously reflect from all such facets of a properly oriented sample, and enter the Detector (DET). This increases the intensity of the electromagnetic beam reflecting from said facets which enters the detector, which electromagnetic radiation can be analyzed as it is substantially similar, in important aspects, to specularly reflected electromagnetic radiation. As indicated in the Disclosure of the Invention Section of this Specification, achieving this result is a primary goal of the present invention. It is noted that simply adjusting the Angle-of-Incidence of a beam of electromagnetic radiation onto a textured surface of a sample, and adjusting the textured sample surface orientation can be undertaken with a goal of simply increasing intensity entering the Detector (DET), without regard to wherefrom on the textured sample surface reflection of electromagnetic radiation into the Detector (DET) occurs. This can lead to acquisition of data which can not be analyzed because too large a component of the electromagnetic radiation received by the Detector (DET) is noisy or depolarized etc. However, where essentially all reflected electromagnetic radiation is from substantially parallel facets, the data acquired is typically very good and its analysis can provide insightful information. It is also noted that if the textured surface of said sample is coated with a thin film, ellipsometric data obtained over a spectroscopic range of wavelengths can be analyzed to evaluate physical and optical properties of said thin film.

FIGS. 4b1 and 4b2 are included to show that a texture pattern can comprise other than grooves as shown in FIGS. 3a-4c, and show, respectively, top and side views of a Sample (SM) which comprises a textured surface with a multiplicity of faceted pyramid shaped structures, with FIG. 4b2 indicating facet texturing can be present on front and back of a sample. This can occur, for instance, where a Sample (SM) is placed into an anisotropic etch bath without protecting the back side thereof. As described in the Disclosure of the Invention Section, the present invention methodology can beneficially make use of data obtained from the backside of such a sample, in evaluating physical and optical properties of a thin film on the front side thereof. Note, data obtained from regions comprising and not comprising a thin film on the one side thereof, or obtained from different, but essentially similar samples which in combination provide both film present and absent regions can be used as well, and all said possibilities should be considered as functionally equivalent.

FIG. 4c shows how orienting the Sample (SM) shown in FIGS. 4b1 and 4b2 much as the Sample (SM) of FIGS. 3a and 3b is oriented in FIG. 4a can lead to increased reflected electromagnetic radiation reflected therefrom toward a detector. For emphasis, note that where a group of substantially parallel facets (a) on a textured Sample (SM) surface are oriented to provide optimum intensity of electromagnetic radiation reflecting therefrom into a Detector (DET) (eg. such as shown in FIGS. 4a and 4c), reflections from other facets which are not so oriented, and for that matter contacts and the like deposited onto the textured surface of the Sample (SM), are directed away from the Detector (DET). See FIG. 3a for instance, which indicates (Scattered) electromagnetic radiation (EM) which is directed away from a Detector (DET) and (EM to Detector) which is reflected thereinto. This is a beneficial result as it reduces scattered reflected components from entering the Detector (DET) and adversely affecting the data provided thereby because of entered noise and depolarizing effects etc.

Figure 3C:
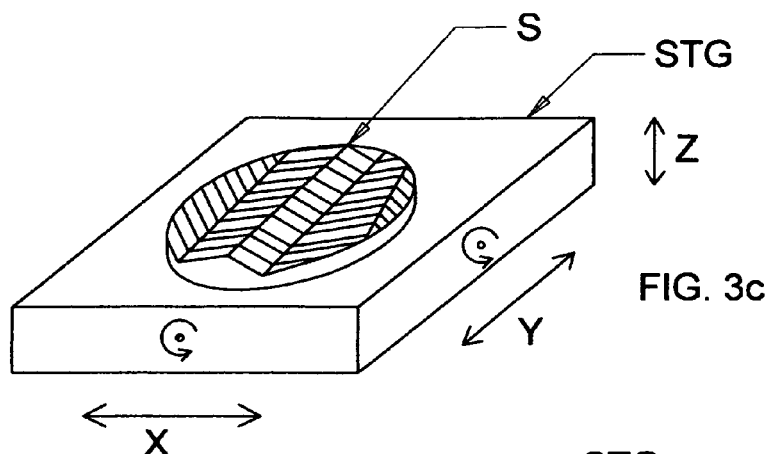
FIGS. 3c-3f are copied from U.S. Pat. No. 7,230,699 and show, respectively, a sample with an irregular surface, a means for orienting the sample of FIG. 3c, and how orienting said sample can control the Angle-of-Incidence to said sample, and therevia increase the amount of electromagnetic radiation reflected therefrom toward a location at which is positioned a detector by controlling the Angle-of-Incidence.
Figure 3D:
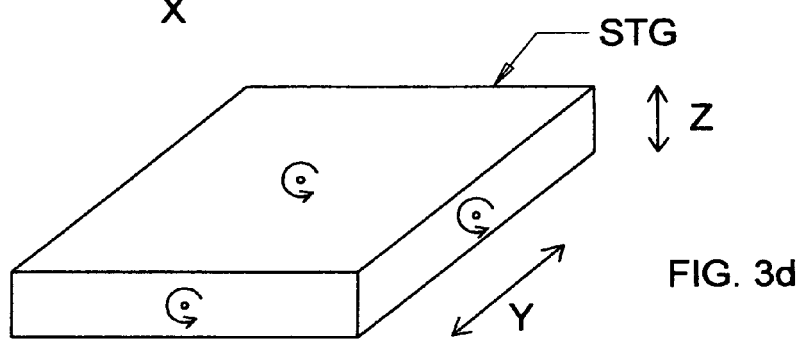
Figure 3E:
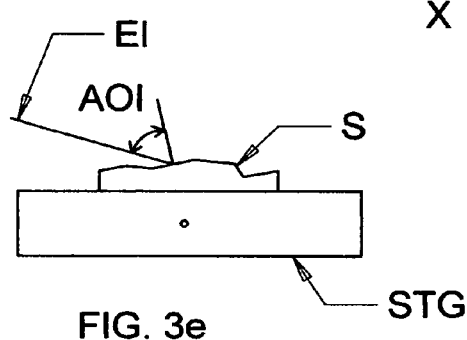
Figure 3F:
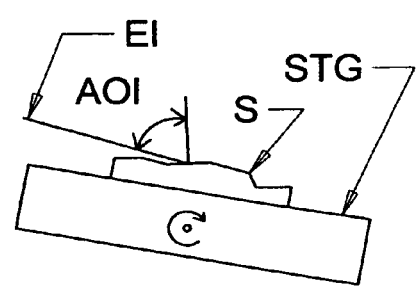
Figure 3G:
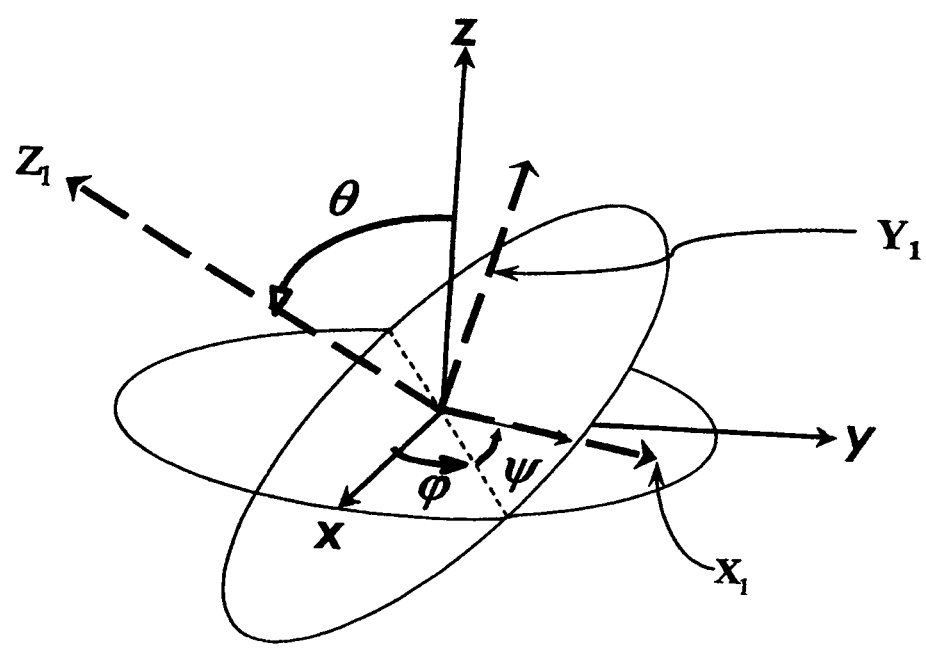
FIG. 3g demonstrates well known Euler Angles, which give insight to how the effect of tilting and rotating a sample can be described conventionally.

FIGS. 3c-3f are copied from U.S. Pat. No. 7,230,699 and are mentioned at this point to demonstrate priority provided by said 699 Patent via CIP status. FIG. 3c shows a sample (S) with an irregular surface. FIG. 3d shows a means (STG) for use in rotatably orienting the sample of FIG. 3c. FIGS. 3e and 3f show how orienting said sample can control the Angle-of-Incidence (AOI) to said Sample (S), and therevia increase the amount of electromagnetic radiation reflected therefrom toward a location at which is positioned a detector by controlling the Angle-of-Incidence (AOI). FIG. 3g is included to demonstrate well known Euler Angles Theta (θ), Phi (φ) and Psi (ψ), which give insight to how the effect of tilting and rotating a sample can be described conventionally. For instance, the Euler Theta (θ) describes Sample (SM) tilt with respect to a Stage (STG) Frame (SF) as said terminology is used herein, and the Euler Phi (φ) describes Sample (SM) rotation in the plane of the Sample (SM) surface.

Figure 5A:
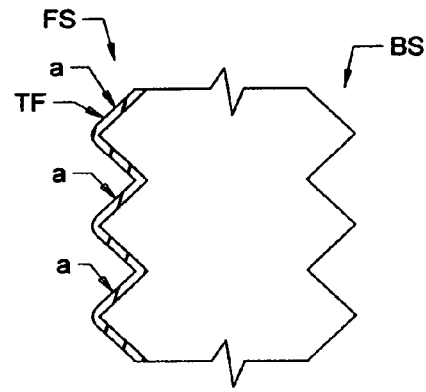
FIG. 5a shows an ellipsometer systems with the stage oriented vertically.
Figure 5A:
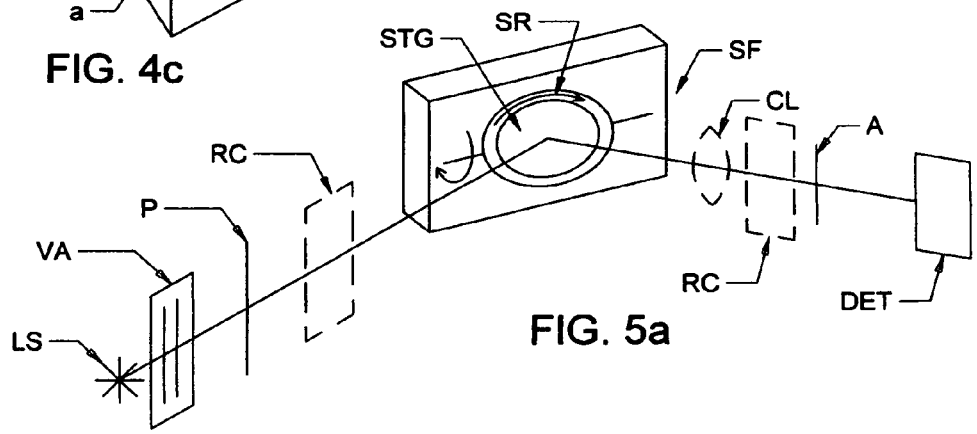

Continuing, FIG. 5a shows an ellipsometer system, much as shown in FIG. 1, but with the Stage (STG) oriented vertically, and being supported by a Stage Frame (SF) and Stage Rotation Means (SR). FIG. 5b better shows how the vertically oriented stage of FIG. 5a. FIG. 5c shows a perspective view of how the Stage (STG) Rotation Effecting Means (SR) and the Stage (STG) per se. of FIGS. 5a and 5b can be rotated in the Stage Frame (SF). FIG. 5d shows a side view of the system in FIG. 5c, with a Sample (SM) mounted to the Stage (STG) per se. Compare FIG. 5d with FIGS. 4a and 4c, with the assumption that the Incident Beam (BI) is approaching said Sample (SM) in a plane perpendicular to the plane of the paper. Note that both rotation of the Stage Rotation Means (RM) in the Stage Frame (SF), and rotation of the Stage (STG) in said Stage Rotation Means (RM) can be applied to optimally orient the Sample (SM) for ellipsometric investigation so that as much as is possible of electromagnetic radiation reflected from the Sample (SM) enters the Detector in FIG. 5a.

The described combination of a Stage Frame (SF), Stage Rotation Means (SR) and Stage (STG) as shown in FIGS. 5a-5d is believed not to have been previously applied in ellipsometer systems to orient textured Samples (SM) therein to enable ellipsometric investigation thereof, where said Sample (SM) orientation is demonstrated in FIGS. 4a and 4c, particularly in the case of where spectroscopic ellipsometry is practiced to investigate a Textured Sample (SM) over a spectrum of wavelengths. This is further the case where ellipsometric data obtained from, for instance, the backside of a Sample (SM) that has texturing on both the Front (FS) and backside (BS) (see FIG. 4b2), but also has a Thin Film (TF) being present only on the Front Side (FS) (see FIG. 4b3), is analyzed by using results obtained by investigating the Back Side (BS) in arriving at physical and optical properties of the Thin Film (TF) on the front side. Such a situation can present in Solar Cell Samples that have an anti-reflective coating on the Front Side (FS) thereof, for instance.

Figure 5E:
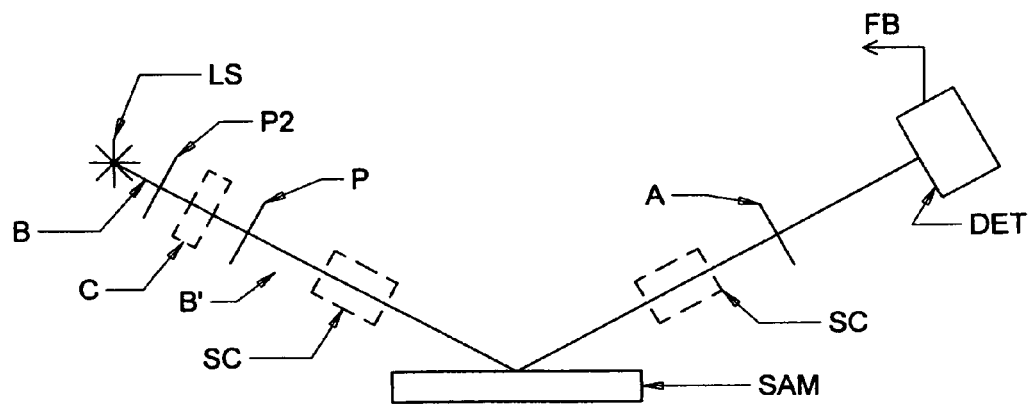
FIG. 5e shows a system for controlling the intensity of a beam of electromagnetic radiation comprising a Source (LS) of a Beam (B) of Electromagnetism, a Control Polarizer (P2), an optional Control Compensator (C), a Beam Polarizer (P), a Sample (SAM), an Analyzer (A) and a Detector (DET).
Figure 5F:
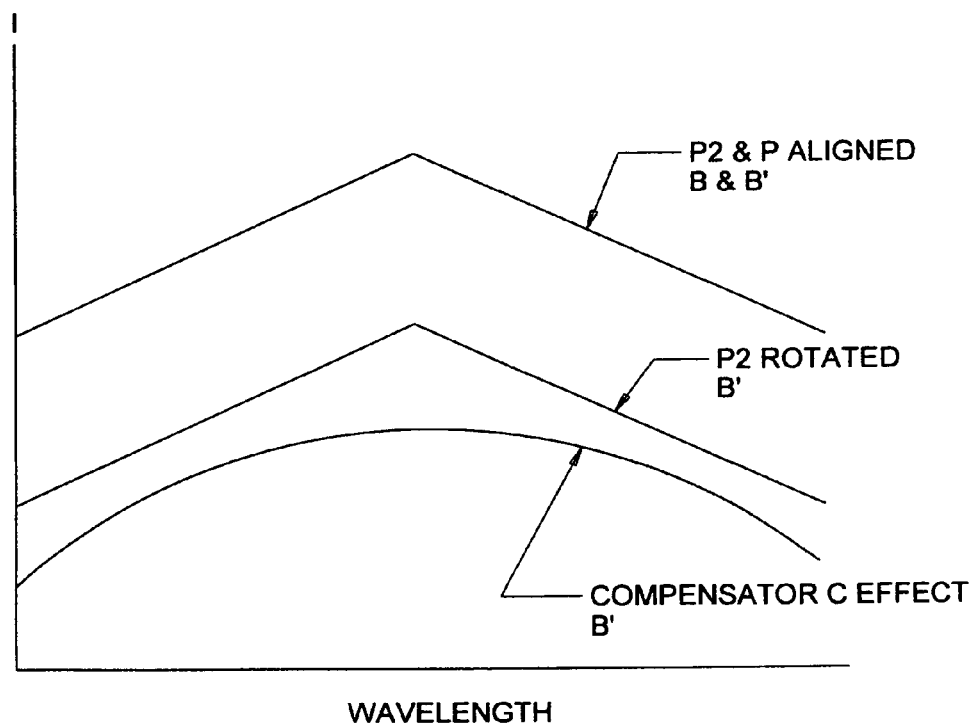
FIG. 5f shows an arbitrary demonstrative effect on Intensity (I) of a Beam (B') as compared to the Intensity of Beam (B) provided by a Source (LS) in FIG. 1.

FIG. 5e shows a Source (LS) of a Beam (B) of Electromagnetism, a Control Polarizer (P2), an optional Compensator (C), a Beam Polarizer (P), a Sample (SAM), an Analyzer (A) and a Detector (DET). FIG. 5f shows an arbitrary demonstrative effect on Intensity (I) of a Beam (B') as compared to the Intensity of Beam (B) provided by a Source (LS). Note the baseline Intensity (I) when said Control and Beam Polarizers (P2) and (P) aligned, and that rotating the Control Polarizer (P2) with respect to the beam Polarizer (P) has a uniform effect over the Wavelength Spectrum. Adding a Control Compensator (C) can cause selective increased attenuation of the mid-wavelength region and provide a more uniform Intensity Spectrum. Note also that at least one System Compensator (SC) can be incorporated into the system. (It is noted that where a Berek-type control compensator, which has its optical axis perpendicular to a surface thereof which a beam enters is used, the terminology "rotation" thereof should be interpreted to mean a tipping thereof to position the optical axis other than parallel to the locus of the beam which passes therethrough, and where the control compensator has its optical axis in the plane of a surface thereof which a beam enters is used, rotation should be interpreted to means an actual rotation about a perpendicular to said surface). It is disclosed that rotation of the control polarizer or compensator can be automated, optionally via a signal in a feedback circuit (FB).

It is noted that the direction of tilt-rotation shown in FIG. 5d can be considered to be positive or negative, and the present invention is sufficiently broad to include a corresponding negative or positive, respectively, tilt-rotation.

It is also noted that any type of ellipsometer or the like can be applied in practicing the methodology of the present invention, such as rotating polarizer, rotating analyzer, rotating compensator, or even phase modulation ellipsometers.

Figure 6A:
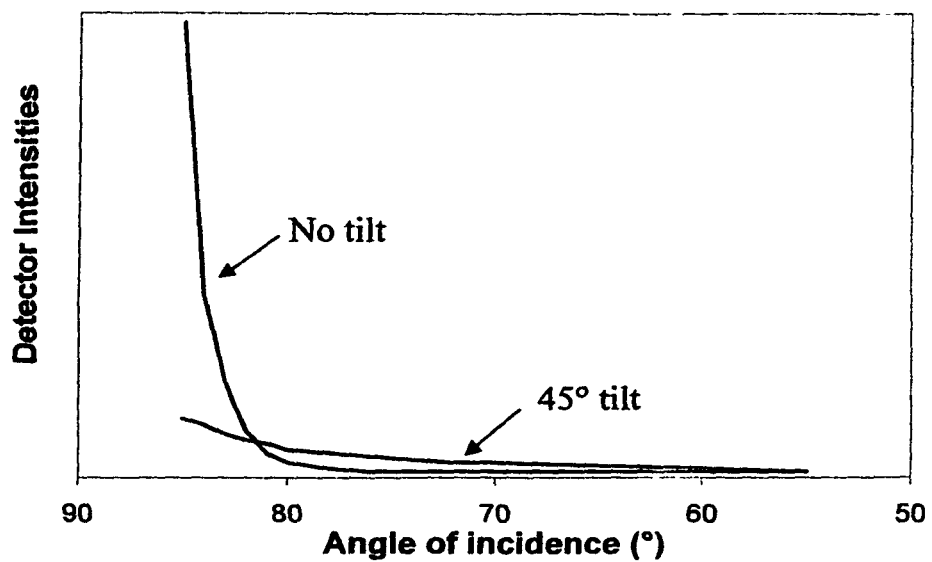
FIG. 6a demonstrates the effect of tilting a sample on intensity.
Figure 6B:
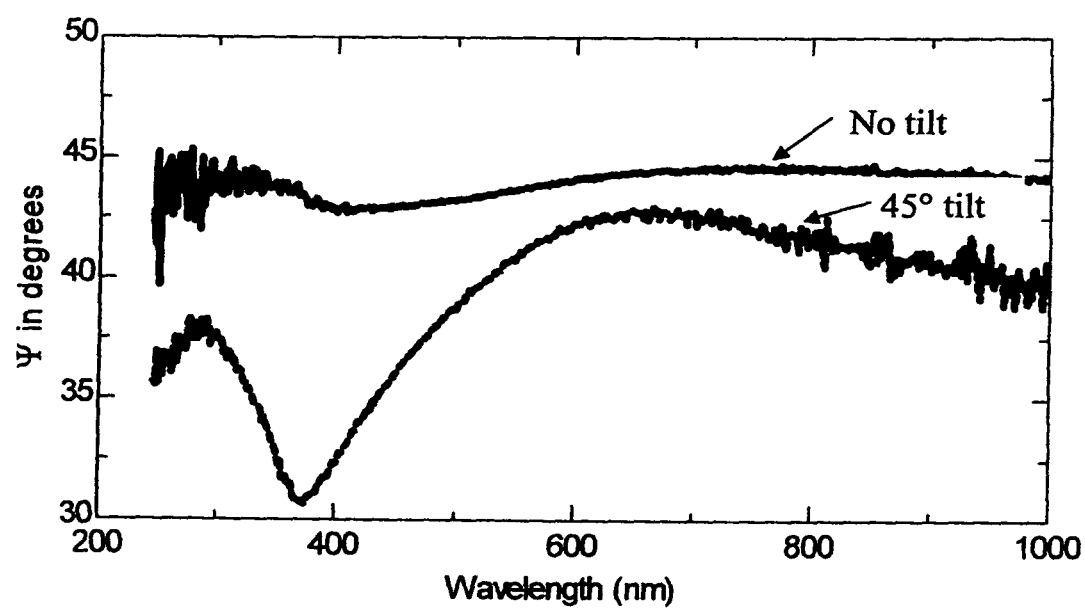
FIG. 6b demonstrates that even though intensity is reduced by sample tilt, the signal to noise ratio is improved.
Figure 6C:
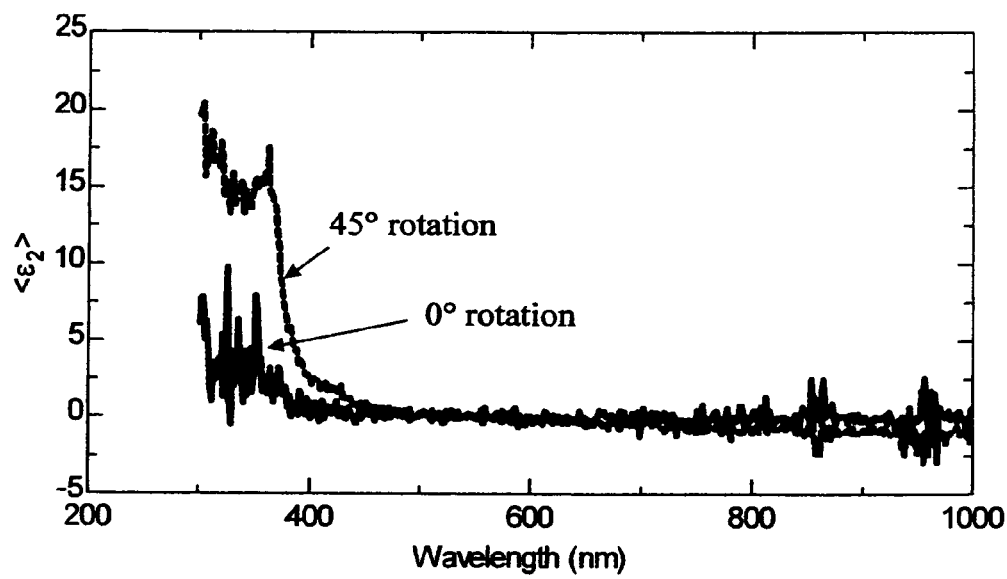
FIG. 6c shows that rotating a sample in the plane of the sample surface can improve the signal to noise ratio.
Figure 6D:
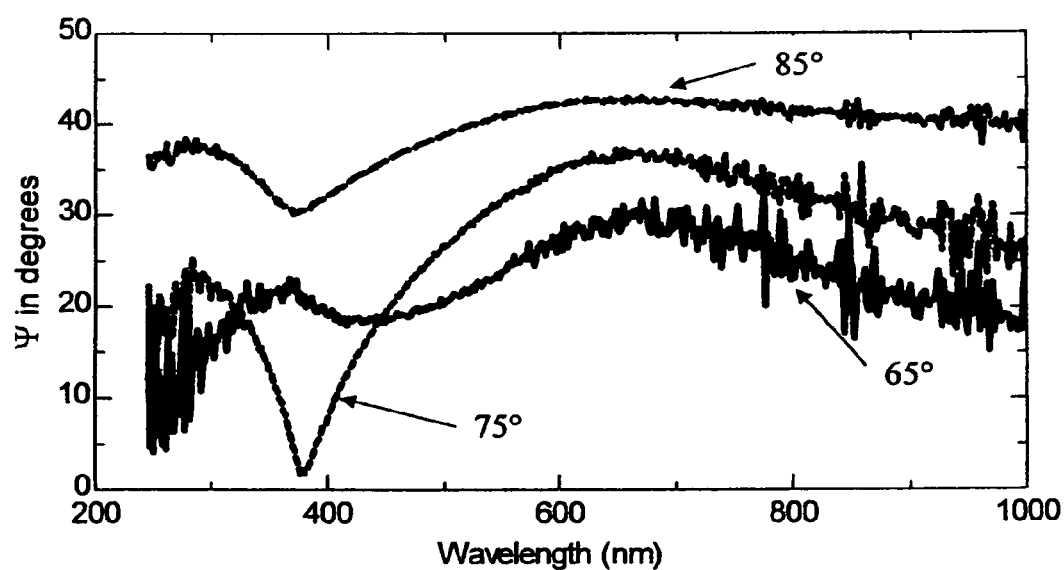
FIG. 6d demonstrates that Angle-of-Incidence can an effect on the signal to noise ratio.

Finally, some exemplary experimentally acquired data is included, in FIGS. 6a-6d, to provide insight to results that were obtained by application of the present invention methodology. FIG. 6a demonstrates the effect of tilting a Textured Sample (SM) with respect to the Stage Frame (SF) plane, (as demonstrated by FIGS. 5c and 5d), on intensity as a function of Angle-of-Incidence (AOI). Note that the intensity a FIG. 5a Detector (DET) receives is significantly decreased by tilting a Sample (SM) by 45 degrees, with respect to the Stage Frame (SF) plane. This alone would not be beneficial, but FIG. 6b demonstrates that even though intensity is reduced by said Sample (SM) tilt, the shown PSI (ψ) signal to noise ratio, (as a function of wavelength), is greatly improved. This is because the diverted intensity reducing electromagnetic radiation is that which scatters from variously oriented facets as opposed to electromagnetic radiation which reflects from a multiplicity of facets which are parallel to one another. That is, even though less signal intensity arrives at the Detector (DET), the signal which is received by the Detector (DET) is of a higher quality, and when analyzed provides superior results. FIG. 6c further shows that rotating a titled Sample (SM), (with a textured surface), in the plane of the Sample (SM) surface, (see FIG. 5c), can also improve signal to noise ratio, (as a function of wavelength). FIG. 6d demonstrates that Angle-of-Incidence (AOI) can also have an affect on the signal to noise ratio in PSI (ψ) data, (as a function of wavelength). Note that at 65 degrees (AOI), as indicated by features of the plot, the data is noisy compared to the better defined PSI (ψ) data achieved at 75 and 85 degrees (AOI). (Note, data quality is indicated by enhanced data plot magnitude change vs. wavelength).

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of improving results achieved by investigating a sample with a textured surface with electromagnetic radiation, said texturing being characterized by a non-random effectively "regular" textured surface and/or a surface characterized by an irregular array of faceted structures; said method comprising:
   a) providing a spectroscopic ellipsometer which comprises:
      a spectroscopic source of a beam of electromagnetic radiation;
      a polarizer;
      a stage system comprising:
         a stage frame oriented in a stage frame plane;
         a stage rotation means; and
         a stage;
      said stage rotation means being rotatably connected to said stage frame in a manner enabling tilting said stage and stage rotation means, as a unit, with respect to said stage frame plane and said stage rotation means enabling rotation of said stage in a plane parallel to the surface of said stage;
      an analyzer; and
      a detector;
   said spectroscopic ellipsometer further comprising at least one selection from the group consisting of:
      a means for controlling beam intensity between the source and detector;
      a variable attenuator for controlling beam intensity between the source and detector;
      a variable attenuator comprising two polarizers which can be adjusted with respect to one another to control the amount of electromagnetic radiation passing therethrough, between the source and detector;
      a sequence of filters for controlling beam intensity between the source and detector; and
      said source of a spectroscopic beam of electromagnetic radiation is a plurality of sources for providing a plurality of beam intensities;
   b) placing a sample with a specularly reflecting surface on said stage so that said specularly reflecting surface faces away from said stage;
   c) while causing said spectroscopic source of a beam of electromagnetic radiation to direct a spectroscopic beam of electromagnetic radiation to pass through said a variable attenuator and polarizer, toward said sample with a specularly reflecting surface, in coordination, adjusting the angle-of-incidence of said spectroscopic beam of electromagnetic radiation with respect to said sample, and the orientation of said sample by adjustment of said stage rotation means adjusting the orientation of said stage and stage rotation means, as a unit, with respect to said stage frame plane, and optionally adjusting said stage rotation to orient the surface of said sample a plane parallel to the surface of said stage, so that the electromagnetic radiation reflected from said sample passes through said analyzer and enters said detector;
   d) adjusting said variable attenuator so that the intensity of the reflected electromagnetic radiation entering said detector does not saturate said detector;
   e) removing said sample with a specular surface from said stage and placing a sample with a textured surface thereupon in its place;
   f) beginning with the setting variable attenuator arrived at in step d, in coordination adjusting the variable attenuator, and the orientation of said textured sample surface by adjustment of said stage rotation means, and tilting said stage and stage rotation means as a unit, with respect to said stage frame plane so that electromagnetic radiation reflected from said sample with a textured surface passes through said analyzer and enters said detector is of a quality to allow analysis thereof, where quality is determined is identified by data magnitude sensitivity to wavelength change or the nature of the electromagnetic beam is enhanced as evidenced by the enabling of determination of at least one selection from the group of ellipsometric PSI and ellipsomtric DELTA therefrom;
   g) with the sample having a textured surface oriented as in step f, obtaining ellipsometric data over a spectroscopic range of wavelengths; and
   h) analyzing said ellipsometric data to evaluate optical and physical properties of said textured sample.

2. A method as in claim 1, wherein the step of providing a spectroscopic ellipsometer further includes providing at least one compensator between the polarizer and analyzer positioned so that the beam of electromagnetic radiation provided by said spectroscopic source of a beam of electromagnetic radiation, which interacts with said textured sample, passes therethrough, and causing said at least one compensator to rotate substantially about the locus of said beam of electromagnetic radiation during the step of obtaining ellipsometric data over a spectroscopic range of wavelengths.

3. A method as in claim 1 wherein the step of placing a sample with a textured surface upon said stage involves placing a sample characterized by the presence of a plurality of facet surfaces which are substantially parallel to one another, and the step of adjusting said stage rotation means, and tilting said stage and stage rotation means as a unit, with respect to said stage frame plane, so that the electromagnetic radiation reflected from said sample with a textured surface passes through said analyzer and enters said detector involves effecting orientation of said sample so that electromagnetic radiation reflecting from said plurality of facet surfaces which are substantially parallel to one another enters said detector, and in which substantially all electromagnetic radiation which does not reflect from said plurality of facet surfaces which are substantially parallel to one another, does not so enter said detector.

4. A method as in claim 3 wherein the textured surface of said sample is coated with a thin film, and in which the steps of obtaining ellipsometric data over a spectroscopic range of wavelengths and analyzing said ellipsometric data to evaluate physical and optical properties of said textured sample involves determining physical and optical properties of said thin film.

5. A method of analyzing physical and optical properties of a thin film on textured surface on a sample front surface, there also being available a similarly textured surface with no thin film present thereupon selected from the group consisting of:
   a textured sample back side surface;
   a region of said textured sample front surface having no thin film present; and
   a similar but different sample having a surface having no thin film present thereupon;
   said texturing being characterized by a non-random effectively "regular" textured surface and/or a surface characterized by an irregular array of faceted structures;
   said method comprising the steps of:
   a) obtaining ellipsometric data from both the thin film comprising textured surface and from the textured surface having no thin film present;
   b) proposing a mathematical/optical model for the thin film comprising textured surface, and a mathematical/optical model for the textured surface having no thin film present;
   c) fitting said ellipsometric data obtained from the textured surface having no thin film present to said mathematical/optical model for said textured surface having no thin film present side to obtain values for sample physical and/or optical properties;
   d) while holding values for the sample physical and/or optical properties determined in step c, fitting said ellipsometric data obtained from the textured surface which comprises a thin film to said mathematical/optical model for said textured surface which comprises a thin film, to obtain values for said thin film physical and optical properties.

6. A method of analyzing physical and optical properties of a thin film on a non-random effectively "regular" textured surface or a surface characterized by an irregular array of faceted structures on a front side surface of a sample having front and back sides, comprising:
   a) providing an ellipsometer or the like system comprising:
      a source of a beam of electromagnetic radiation;
      a polarizer;
      a stage system comprising:
         a stage frame oriented in a stage frame plane;
         a stage rotation means; and
         a stage;
         said stage rotation means being rotatably connected to said stage frame in a manner enabling tilting said stage and stage rotation means, as a unit, with respect to said stage frame plane and said stage rotation means enabling rotation of said stage in a plane parallel to the surface of said stage;
      an analyzer; and
      a detector;
   said spectroscopic ellipsometer optionally further comprising at least one beam intensity controller selected from the group consisting of:
      a means for controlling beam intensity between the source and detector;
      a variable attenuator for controlling beam intensity between the source and detector;
      a variable attenuator comprising two polarizers which can be adjusted with respect to one another to control the amount of electromagnetic radiation passing therethrough, between the source and detector;
      a sequence of filters for controlling beam intensity between the source and detector; and
      said source of a spectroscopic beam of electromagnetic radiation is a plurality of sources for providing a plurality of beam intensities;
   b) positioning a sample with a non-random effectively "regular" textured surface or a surface characterized by an irregular array of faceted structures on a sample front side surface onto said stage with a thin film on said front surface side of said sample facing away from said stage;
   c) causing a beam of electromagnetic radiation, provided by said source of a beam of electromagnetic radiation, to pass through said polarizer, impinge on and reflect from said front surface side of said sample, pass through said analyzer and enter said detector;
   d) effecting a stage and stage rotation means tilt to orient said front side surface of said sample having a thin film thereupon in a plane oriented at between 10-90 degrees with respect to the plane of said stage frame;
   e) while monitoring detector data output, causing said stage rotation means to rotate the textured sample in the plane parallel to the surface of said stage until said data output is of a sufficient quality to allow beneficial analysis thereof, as evidenced by the enabling of determination of at least one selection from the group of ellipsometric PSI and ellipsomtric DELTA therefrom;
   f) optionally repeating steps d and e using different stage and stage rotation means tilts to orient said sample front side surface having a thin film thereupon in a different plane oriented at between 10-90 degrees with respect to the plane of said stage frame, until a best combination of stage and stage rotation means tilt, and stage rotation in the plane parallel to the surface of said stage is determined based on data output is of a nature to allow beneficial analysis thereof, as evidenced by the enabling of determination of at least one selection from the group of ellipsometric PSI and ellipsomtric DELTA therefrom;
   g) obtaining data from said detector
   said method further comprising:
   h) positioning said sample onto said stage with the thin film on said front surface side of said sample facing toward said stage so that the sample back side thereof faces away from said stage;
   i) causing a beam of electromagnetic radiation, provided by said source of a beam of electromagnetic radiation, to pass through said polarizer, impinge on and reflect from said sample back side, pass through said analyzer and enter said detector;

j) effecting a stage and stage rotation means tilt to orient said sample back side surface facing away from said stage in a plane oriented at between 10-90 degrees with respect to the plane of said stage frame;
k) while monitoring detector data output, causing said stage rotation means to rotate the textured sample in the plane parallel to the surface of said stage until said data output is of a sufficient quality to allow beneficial analysis thereof, as evidenced by the enabling of determination of at least one selection from the group of ellipsometric PSI and ellipsomtric DELTA therefrom;
l) optionally repeating steps j and k using different stage and stage rotation means tilts to orient said sample back side surface facing away from said stage as oriented in a different plane oriented at between 10-90 degrees with respect to the plane of said stage frame, until a best combination of stage and stage rotation means tilt, and stage rotation in the plane parallel to the surface of said stage is determined based on data output is of a nature to allow beneficial analysis thereof, as evidenced by the enabling of determination of at least one selection from the group of ellipsometric PSI and ellipsomtric DELTA therefrom;
m) obtaining data from said detector;
n) simultaneously analyzing detector data collected in step g when the front side surface comprising a thin film is facing away from said stage, and detector data collected in step m the front surface side is facing toward said stage, to determine physical and/or optical properties of said thin film on said sample front side surface.

7. A method as in claim 6, in which the at least one beam intensity controller is present and is adjusted during practice of the method to prevent saturation of the detector output.

\* \* \* \* \*